US012704421B2

(12) United States Patent
Lynch et al.

(10) Patent No.: US 12,704,421 B2
(45) Date of Patent: Aug. 11, 2026

(54) CONFORMABLE THIN FILM-BASED STRAIN SENSING WITH FLEXIBLE SUBSTRATE

(71) Applicant: The Regents of the University of Michigan, Ann Arbor, MI (US)

(72) Inventors: Jerome P. Lynch, Ann Arbor, MI (US); Peng Sun, Ann Arbor, MI (US); Andrew Robert Burton, New York, NY (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1298 days.

(21) Appl. No.: 17/613,415

(22) PCT Filed: May 29, 2020

(86) PCT No.: PCT/US2020/035321
§ 371 (c)(1),
(2) Date: Nov. 22, 2021

(87) PCT Pub. No.: WO2021/034368
PCT Pub. Date: Feb. 25, 2021

(65) Prior Publication Data

US 2022/0221350 A1 Jul. 14, 2022

Related U.S. Application Data

(60) Provisional application No. 62/855,483, filed on May 31, 2019.

(51) Int. Cl.
*G01L 1/06* (2006.01)
*A61B 5/00* (2006.01)
(Continued)

(52) U.S. Cl.
CPC ............ *G01L 1/144* (2013.01); *A61B 5/4504* (2013.01); *A61B 5/4851* (2013.01);
(Continued)

(58) Field of Classification Search
CPC ..... G01L 1/06; G01L 1/18; G01L 1/20; G01L 1/22
See application file for complete search history.

(56) References Cited

U.S. PATENT DOCUMENTS

2006/0170535 A1 8/2006 Watters et al.
2007/0107528 A1 5/2007 Schroeder et al.
(Continued)

OTHER PUBLICATIONS

Albrektsson T, Johansson C., Osteoinduction, osteoconduction and osseointegration, Eur Spine J. 2001; 10(2):S96-S101, doi:10.1007/s005860100282.

(Continued)

*Primary Examiner* — Peter J Macchiarolo
*Assistant Examiner* — Eric S McCall
(74) *Attorney, Agent, or Firm* — Lempia Summerfield Katz LLC

(57) ABSTRACT

A strain sensor includes a flexible substrate and a circuit disposed on the flexible substrate. The circuit includes an inductance to receive an excitation signal, the circuit being configured to generate a radio frequency response to the excitation signal via the inductance. The circuit includes an elongated trace coupled to the inductance and configured to bend and stretch longitudinally upon deformation of the flexible substrate. The elongated trace includes a non-uniformity configured such that the elongated trace deforms and tears at the non-uniformity and exhibits a non-linear increase in resistance as a tensile strain to which the elongated trace is subjected reaches a strain threshold. The non-linear
(Continued)

increase in resistance modifies a characteristic of the radio frequency response of the circuit.

18 Claims, 21 Drawing Sheets

(51) Int. Cl.

| | |
|---|---|
| ***G01L 1/10*** | (2006.01) |
| ***G01L 1/14*** | (2006.01) |
| ***H05K 1/16*** | (2006.01) |

(52) U.S. Cl.

CPC ............ *A61B 5/6878* (2013.01); *G01L 1/106* (2013.01); *H05K 1/162* (2013.01); *H05K 1/165* (2013.01); *H05K 1/167* (2013.01); *A61B 2562/164* (2013.01); *H05K 2201/0154* (2013.01); *H05K 2201/10098* (2013.01)

(56) References Cited

U.S. PATENT DOCUMENTS

| | | | |
|---|---|---|---|
| 2009/0121872 A1 | 5/2009 | Lynch et al. | |
| 2011/0023620 A1 | 2/2011 | Clothier et al. | |
| 2013/0041235 A1 | 2/2013 | Rogers et al. | |
| 2015/0016487 A1* | 1/2015 | Britton | G01L 1/205 374/185 |
| 2015/0276372 A1* | 10/2015 | Tata | C23C 14/5813 351/158 |
| 2015/0296607 A1* | 10/2015 | Yang | H05K 1/167 361/749 |
| 2015/0313745 A1 | 11/2015 | Cheng | |
| 2016/0231097 A1 | 8/2016 | Lynch et al. | |
| 2017/0150896 A9 | 6/2017 | Lu et al. | |
| 2020/0232970 A1* | 7/2020 | Haick | G01K 7/186 |
| 2020/0352505 A1 | 11/2020 | Lynch et al. | |
| 2025/0327652 A1* | 10/2025 | Qiu | G01L 1/22 |

OTHER PUBLICATIONS

Branemark PI, Adell R, Albrektsson T, Lekholm U, Lundkvist S, Rockler B, Osseointegrated titanium fixtures in the treatment of edentulousness, Biomaterials vol. 4. 1983, 25-28. doi: 10.1016/B978-008045154-1.50003-4.

Burton A et al., Bio-compatible wireless inductive thin-film strain sensor for monitoring the growth and strain response of bone in osseointegrated prostheses; Structural Health Monitoring; 2019; doi: 10.1177/1475921719831452.

Caizzone S, DiGiampaolo E., Wireless Passive RFID Crack Width Sensor for Structural Health Monitoring, IEEE Sens Journal, 2015, 6767-6774, doi:10.1109/JSEN.2015.2457455.

Cho C, Yi X, Li D, Wang Y, Tentzeris MM, Passive frequency doubling antenna sensor for strain and crack detection, IEEE Sens Journal, 2016; 16(14), 5725-5733. doi:10.1115/SMASIS2012-7923.

D. W. Greve, I. J. Oppenheim, and A. F. Chen, An instrumented intramedullary implant to monitor strain in fracture healing, IEEE Int. Ultrason. Symp. IUS, pp. 1220-1223, 2012.

Dhert WJA, Thomsen P, Blomgren AK, Esposito M, Ericson LE, Verbout AJ, Integration of press-fit implants in cortical bone: A study on interface kinetics, J Biomed Mater Res. 1998; 41(4), 574-583.

Dion MK et al., Smart Orthopaedic Implants: Applications in Total Knee Arthroplasty, American Journal Eng Appl Sciences, 2016; 9(4), 1232-1238, doi:10.3844/ajeassp.2016.1232.1238.

F. Burny et al., Concept, design and fabrication of smart orthopedic implants, Med. Eng. Phys., vol. 22, No. 7, pp. 469-479, 2000.

F. Umbrecht, P. Wagli, S. Dechand, F. Gattiker, J. Neuenschwander, U. Sennhauser, and C. Hierold, Wireless implantable passive strain sensor: design, fabrication and characterization, J. Micromechanics Microengineering, vol. 20, No. 8, p. 85005, 2010.

HD Microsystems; Product Bulletin PI 2525, PI 2555 & PI 2574; 2012.

Healey JH, Morris CD, Athanasian EA, Boland PJ, Compress@ knee arthroplasty has 80% 10-year survivorship and novel forms of bone failure; Clin Orthop Relat Res. 2013; 471(3): 774-783, doi:10.1007/s11999-012-2635-6.

International Preliminary Report on Patentability cited in corresponding app. No. PCT/US2020/035321; Nov. 16, 2021; 8 pp.

International Search Report and Written Opinion cited in corresponding application No. PCT/US2020/035321; Feb. 9, 2021; 9pp.

Jia Y, Sun K, Agosto FJ, Quiñones MT, Design and characterization of a passive wireless strain sensor, Meas Sci Technol., 2006; 17(11), 2869-2876, doi:10.1088/0957-0233/17/11/002.

Kalansuriya P, Bhattacharyya R, Sarma S., RFID tag antenna-based sensing for pervasive surface crack detection, IEEE Sens. Journal, 2013; 13(5), 1564-1570, doi:10.1109/JSEN.2013.2240155.

Kim J, Wang Z, Kim WS, Stretchable RFID for wireless strain sensing with silver nano ink, IEEE Sens Journal, 2014; 14(12), 4395-4401. doi:10.1109/JSEN.2014.2335743.

Kramer MJ, Tanner BJ, Horvai AE, O'Donnell RJ, Compressive osseointegration promotes viable bone at the endoprosthetic interface: Retrieval study of Compress® implants, Int Orthop. 2008; 32(5):567-571, doi:10.1007/s00264-007-0392-z.

L. A. Korduba et al., Radio Frequency Identification as a Testbed for Integration of Low Frequency Radio Frequency Sensors Into Orthopedic Implants, J. Med. Device., vol. 7, No. 1, p. 11008, 2013.

Leijendekkers RA et al., Comparison of bone-anchored prostheses and socket prostheses for patients with a lower extremity amputation: a systematic review. Disabil Rehabil. 2017; 39(11):1045-1058. doi:10.1080/09638288.2016.1186752.

Lynch JP, Farrar CR, Michaels JE, Structural health monitoring: Technological advances to practical implementations, Proc IEEE, 2016; 104(8); 1508-1512, doi:10.1109/JPROC.2016.2588818.

Mohan SS, del Mar Hershenson M, Boyd SP, Lee TH, Simple accurate expressions for planar spiral inductances, IEEE J Solid-State Circuits, 1999; 34(10), 1419-1424.

Ortiz-Catalan M, Håkansson B, Branemark R, An osseointegrated human-machine gateway for long-term sensory feedback and control of artificial limbs, Sci Transl Med. 2014; 6(257); 1-9.

R. Melik, E. Unal, N. K. Perkgoz, B. Santoni, D. Kamstock, C. Puttlitz, and H. V. Demir, Nested Metamaterials for Wireless Strain Sensing, IEEE J. Sel. Top. Quantum Electron., vol. 16, No. 2, pp. 450-458, 2010.

Rydell NW, Forces Acting on the Femoral Head-Prosthesis: A Study on Strain Gauge Supplied Prostheses in Living Persons, Acta Orthop Scand., 1966; 37(sup88), 1-132. doi: 10.3109/ort.1966.37.suppl-88.01.

S. Jönsson, K. Caine-Winterberger, and R. Brånemark, Osseointegration amputation prostheses on the upper limbs: methods, prosthetics and rehabilitation, Prosthet. Orthot. Int., vol. 35, No. 2, pp. 190-200, 2011.

Seo JM, Kim SJ, Chung H, Kim ET, Yu HG, Yu YS, Biocompatibility of polyimide microelectrode array for retinal stimulation, Mater Sci Eng C.; 2004; 24(1-2), 185-189. doi:10.1016/j.msec.2003.09.019.

Silva NM, Santos PM, Ferreira JAF, et al. Power management architecture for smart hip prostheses comprising multiple energy harvesting systems, Sensors Actuators A Phys.; 2013; 202; 183-192; doi:10.1016/j.sna.2013.01.049.

Stein M., Intelligent Implants: Sensors and More in Orthopedic Devices, Orthopaedic Proceedings. vol. 95-B. British Editorial Society of Bone and Joint Surgery; 2013, 538-538.

W. K. Tyler et al., Compress Periprosthetic Fractures: Interface Stability and Ease of Revision, Clin. Orthop. Relat. Res., vol. 467, No. 11, pp. 2800-2806, 2009.

Wood SL, Neikirk DP, Passive sensors for infrastructure monitoring, Structures and Materials, vol. 7292; 2009, 729202, doi:10.1117/12.821722.

Xu W, Robinson K, X-ray image review of the bone remodeling around an osseointegrated trans-femoral implant and a finite element simulation case study, Annals Biomed Eng. 2008; 36(3), 435-443, doi:10.1007/s10439-007-9430-7.

(56) References Cited

OTHER PUBLICATIONS

Yi X, Cho C, Cooper J, Wang Y, Tentzeris MM, Leon RT, Passive wireless antenna sensor for strain and crack sensing—electromagnetic modeling, simulation, and testing, Smart Mater Struct., 2013, 22(8), 085009, doi:10.1088/0964-1726/22/8/085009.
Zhang Y, Bai L, Rapid structural condition assessment using radio frequency identification (RFID) based wireless strain sensor, Autom Constr., 2015; 54:1-11, doi:10.1016/j.autcon.2015.02.013.

* cited by examiner

Figure 2
a1. bond PI film on Si wafer
a2. pattern bottom Au layer
a3. spin-coat PI dielectric layer
a4. etch PI with Al etch mask
a5. pattern top Au layer
a6. lift film from Si wafer
b1. bond PI film (with Cu cladding) on Si wafer
b2. spin and pattern photoresist
b3. lift film and etch copper on both sides
b4. rebond film to wafer and strip photoresist
b5. encase with PI coating
b6. lift film from Si wafer
c1. bond PI film on Si wafer
c2. pattern metal stack (Au+Ti)
c3. spin and pattern photoresist etch mask
c4. etch Au
c5. strip photoresist
c6. lift film from Si wafer

CONFORMABLE THIN FILM-BASED STRAIN SENSING WITH FLEXIBLE SUBSTRATE

CROSS-REFERENCE TO RELATED APPLICATION

This U.S. National Phase application is based on International Application No. PCT/US2020/035321, filed May 29, 2020, which claims the benefit of U.S. provisional application entitled "Conformable Thin Film-Based Strain Sensing with Flexible Substrate," filed May 31, 2019, and assigned Ser. No. 62/855,483, the entire disclosures of which is are hereby expressly incorporated by reference. Priority benefit of these earlier filed applications is hereby claimed.

STATEMENT REGARDING FEDERALLY SPONSORED RESEARCH OR DEVELOPMENT

This invention was made with government support under Contract No. N00014-16-1-2738 awarded by the Office of Naval Research. The government has certain rights in the invention.

BACKGROUND OF THE DISCLOSURE

Field of the Disclosure

The disclosure relates generally to strain sensors.

Brief Description of Related Technology

Osseointegrated prostheses are useful for amputees for whom traditional socket prostheses are not a viable option. Osseointegration offers many benefits, such as enhanced amputee comfort, sensory feedback during limb use, and the perception of the prosthesis being a natural part of the body.

Osseointegrated prosthetic limbs utilize metallic (typically titanium) fixtures implanted into bone with one end of the fixture extending outside the limb where an artificial limb is attached. Commercially available osseointegrated prostheses use screw, press fit, and compression implantation to fixate a prosthesis. In a compression-type fixture, an anchor is placed within the inner cavity of reamed bone with a spindle at the bone end attached to the anchor via a threaded rod. Post-tensioning of the rod during surgical implantation results in a permanent compression to the host bone thereby stimulating and accelerating bone growth. Studies on 2 to 3 cm diameter bone reveals the thickness of the bone in the compression zone after surgical placement can increase as much as 1 mm after 79 months. This is equivalent to a 5 to 10% increase in the circumference of the bone.

Osseointegration also has a number of challenges. First, it is difficult to determine when sufficient osseointegration has occurred. As a result, it is difficult to decide when to allow the fixture to be loaded, which leads to conservative approaches to post-operative recovery. For example, X-rays can be used to image bone growth, but the images do not give complete evidence of osseointegration, making it difficult to decide when sufficient osseointegration has occurred. Another challenge is the skin of the limb does not naturally bond to the percutaneous extension of the prosthesis. This leaves an entry point for bacteria that can infect tissue or bone. Also, bone can develop fractures due to excessive load on the prosthesis.

The field of orthopedics utilizes implantable devices to assist patients with bone healing (e.g., fixators) and for the replacement of joints. Some implants include sensors in an effort to provide data related to the performance of the implant. Burny et al., "Concept, design and fabrication of smart orthopedic implants," Med Eng Phys. 2000; 22(7): 469-479, describes a strain monitoring system for smart orthopedic implants in which wireless inductive coupling delivers energy to, and reads data from, an implanted sensor using an external reader. Korduba et al., "Radio Frequency Identification as a Testbed for Integration of Low Frequency Radio Frequency Sensors Into Orthopedic Implants," J Med Device. 2013; 7(1):11008 describes miniaturized radio frequency identification (RFID) platforms for in vivo application, in which compact devices use commercial RFID solutions embedded into glass or ceramic packages. Dion et al., "Smart Orthopaedic Implants: Applications in Total Knee Arthroplasty," Am J Eng Appl Sci. 2016; 9(4):1232-1238 describes a capacitive element included in a wireless inductive circuit to measure strain in the implant associated with total knee arthroplasty. The circuit provided an 11 mm diameter copper coil encased in parylene and embedded directly into the implant. These in vivo wireless sensing solutions are integrated into the implant design. But such integration into the implant leads to undesirably higher implant costs.

Structural health monitoring (SHM) is a field in which thin film sensors have been used for monitoring structural strain and damage states. Thin film sensors can deform with the structure on which the sensors are installed, providing the sensors with a high degree of versatility. The sensors are also designed to be flexible and are therefore not prone to the same brittle failures observed in rigid counterparts. The sensors have been designed as passive circuits with wireless inductive elements that receive power from and communicate data to a reader.

Sensors have been used for wireless strain sensing and crack detection in thin film assemblies. Specific to identifying cracks or peak strain in structures, wireless passive sensing solutions have been described in which a sensing component is designed to fail under a specific damage state (e.g., corrosion, cracking). A failed sensing component can provide an unambiguous change in the electrical properties of the sensor leading to robust detection of the damage event. For example, Wood et al., "Passive sensors for infrastructure monitoring," Sensors and Smart Structures Technologies, Vol 7292; 2009:729202 illustrates wireless sensing with two RFID circuits, one of which is a reference circuit and the other is a sensor for detecting corrosion. Zhang et al., "Rapid structural condition assessment using radio frequency identification (RFID) based wireless strain sensor," Autom. Constr. 2015; 54:1-11 describes a "breakage-triggered" sensor where an acrylic bar is used as a brittle fuse in an RFID circuit designed to detect peak strain. Both of these examples use wireless passive sensors to detect limit states in a structure.

SUMMARY OF THE DISCLOSURE

In accordance with one aspect of the disclosure, a strain sensor includes a flexible substrate and a circuit disposed on the flexible substrate. The circuit includes an inductance to receive an excitation signal, the circuit being configured to generate a radio frequency response to the excitation signal via the inductance. The circuit includes an elongated trace coupled to the inductance and configured to bend and stretch longitudinally upon deformation of the flexible substrate.

The elongated trace includes a non-uniformity configured such that the elongated trace deforms and tears at the non-uniformity and exhibits a non-linear increase in resistance as a tensile strain to which the elongated trace is subjected reaches a strain threshold. The non-linear increase in resistance modifies a characteristic of the radio frequency response of the circuit.

In accordance with another aspect of the disclosure, a method of sensing hoop strain in connection with an object. The method includes applying a strain sensor around a periphery of the object, the strain sensor including a flexible substrate and a circuit disposed on the flexible substrate, the circuit including an inductance, the circuit including an elongated trace coupled to the inductance, the elongated trace bending as the strain sensor is applied around the periphery of the object, the elongated trace including a non-uniformity configured such that the elongated trace tears at the non-uniformity and exhibits a non-linear increase in resistance as the hoop strain reaches a strain threshold. The method further includes directing an excitation signal to the inductance, the excitation signal causing the circuit to generate a radio frequency response via the inductance, and monitoring the radio frequency response for a change in a characteristic of the radio frequency response to detect the non-linear increase in the resistance.

In accordance with yet another aspect of the disclosure, a method of fabricating a strain sensor includes patterning a plurality of metal layers on a flexible substrate to form a circuit on the flexible substrate, the circuit including an inductor and an elongated trace coupled to the inductor, and removing metal from a portion of the elongated trace to define a non-uniformity such that the elongated trace is configured to tear at the non-uniformity as the elongated trace is subjected to a tensile strain.

In accordance with still another aspect of the disclosure, a system includes a flexible substrate, a first resistive-inductive-capacitive (RLC) circuit disposed on the flexible substrate, the first RLC circuit including a structural fuse and an inductor coupled to the structural fuse, and a second RLC circuit disposed on the flexible substrate, the second RLC circuit including a capacitor and an inductor coupled to the capacitor. The first and second RLC circuits have different resonant frequencies such that states of the structural fuse and the capacitor are ascertainable via analyses of respective responses of the first and second RLC circuits.

In connection with any one of the aforementioned aspects, the systems, devices, and/or methods described herein may alternatively or additionally include any combination of one or more of the following aspects or features. The non-uniformity includes a non-uniform composition of the trace. The non-uniformity includes a non-uniform thickness of the trace. The elongated trace includes a plurality of metal layers. At least one metal layer of the plurality of metal layers is not present at the non-uniformity. The elongated trace includes a conduction metal layer and an adhesion metal layer disposed between the conduction metal layer and the flexible substrate. The conduction metal layer is not present at the non-uniformity such that the elongated trace has a thickness at the non-uniformity that corresponds with a thickness of the adhesion metal layer. The trace is disposed along a curve arising from the deformation of the flexible substrate such that the tensile strain is a hoop strain. The circuit further includes a capacitance, both the inductance and the capacitance being disposed in series with the elongated trace. The inductance and the capacitance are positioned such that the deformation of the flexible substrate does not modify the inductance and the capacitance. The characteristic of the radio frequency response is a phase of the radio frequency response generated by the circuit in response to the excitation signal. The strain sensor further includes a further circuit disposed on the flexible substrate, the further circuit including an inductor and a capacitor. The inductor is configured to receive the excitation signal. The capacitor includes a parallel plate arrangement. The parallel plate arrangement is configured such that a radio frequency response of the further circuit to the excitation signal is modified by strain arising from further deformation of the substrate and the capacitor. The flexible substrate includes a section on which the inductance is disposed and an elongated strip extending outward from the section, the elongated trace being disposed on the elongated strip. The elongated trace includes a conductive loop disposed on the elongated strip. The flexible substrate includes a biocompatible polymer substrate. Applying the strain sensor includes affixing ends of an elongated strip of the flexible substrate to the object, the elongated trace being disposed on the elongated strip. Directing the excitation signal includes generating the excitation signal across a range of frequencies. Monitoring the radio frequency response includes evaluating the radio frequency response to detect when the change in the characteristic of the radio frequencies occurs. The characteristic of the radio frequency response includes a phase of the radio frequency response. Applying the strain sensor includes wrapping the strain sensor around a bone such that the hoop strain is indicative of circumferential bone growth. A composite metal layer of the plurality of metal layers includes a stack of constituent metal layers. Removing the metal includes removing a conduction metal layer of the stack of constituent metal layers to expose an adhesion metal layer of the stack of constituent metal layers at the non-uniformity. The method further includes removing a sacrificial substrate by which the flexible substrate is supported during the plurality of metallization procedures. Each metal layer of the plurality of metal layer is composed of at least one biocompatible metal. The flexible substrate is composed of a biocompatible polymer. The system further includes a reader configured to interrogate the states of the structural fuse and the capacitor via inductive coupling with the inductors of the first and second RLC circuits, respectively. The reader is configured to generate an excitation signal across a range of frequencies and to determine when respective changes in a characteristic of the respective responses of the first and second RLC circuits to the excitation signal occur to determine the states of the structural fuse and the capacitor. The first circuit includes an elongated trace along which the structural fuse is disposed. The flexible substrate includes a section on which the inductor of the first RLC circuit is disposed and an elongated strip extending outward from the section. The structural fuse is disposed on the elongated strip.

BRIEF DESCRIPTION OF THE DRAWING FIGURES

For a more complete understanding of the disclosure, reference should be made to the following detailed description and accompanying drawing figures, in which like reference numerals identify like elements in the figures.

FIG. 1(*b*) is a schematic view of the strain sensing system of FIG. 1 to depict application of a strain sensor of the strain sensing system to a bone in accordance with one example.

FIG. 1(*c*) is a schematic, plan view of the strain sensor of FIG. 2.

Figures 4A, 4B, 4C:
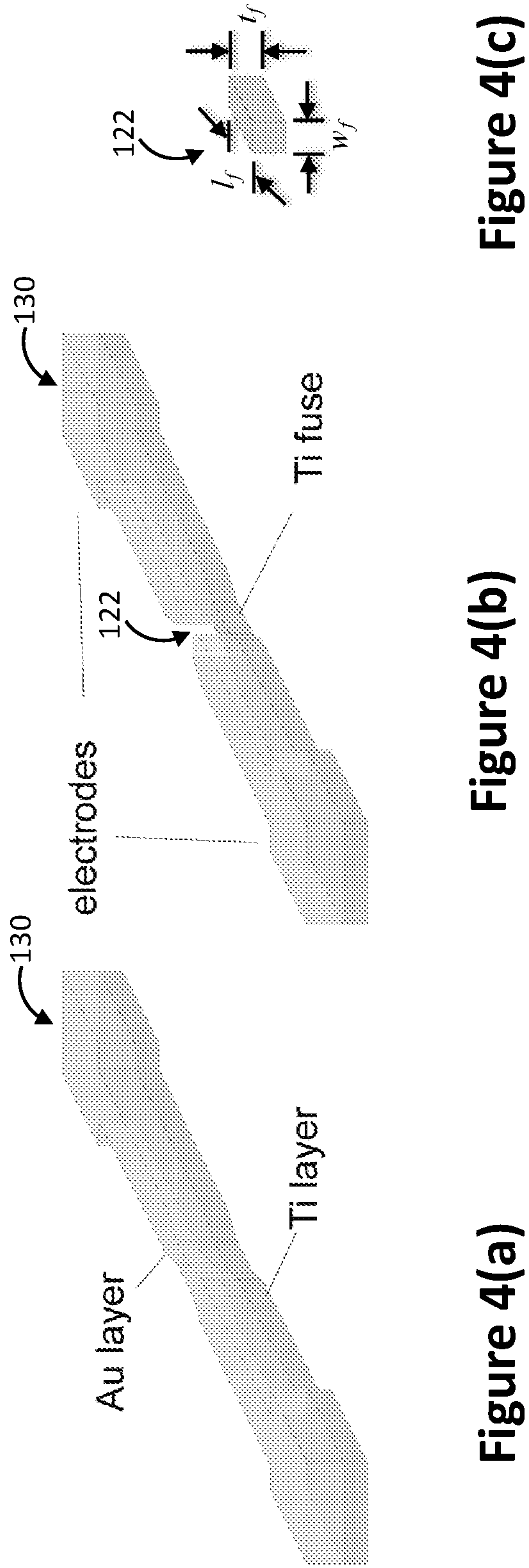
Figure 5A:
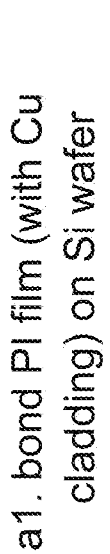
Figure 5A:
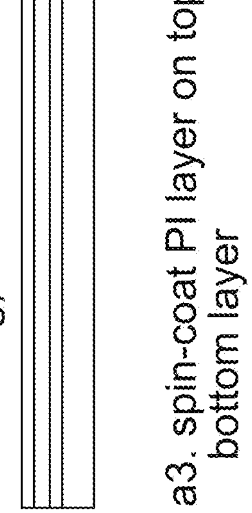
Figure 5A:
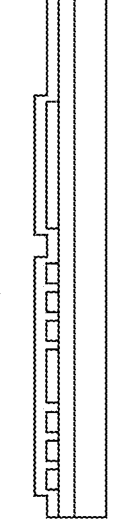
Figure 5A:
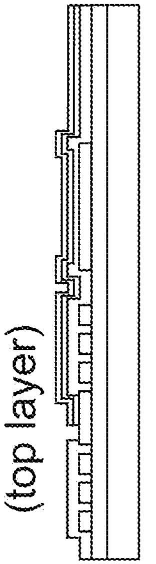
Figure 5A:
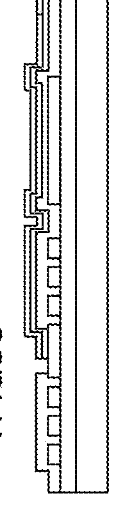
Figure 5B:
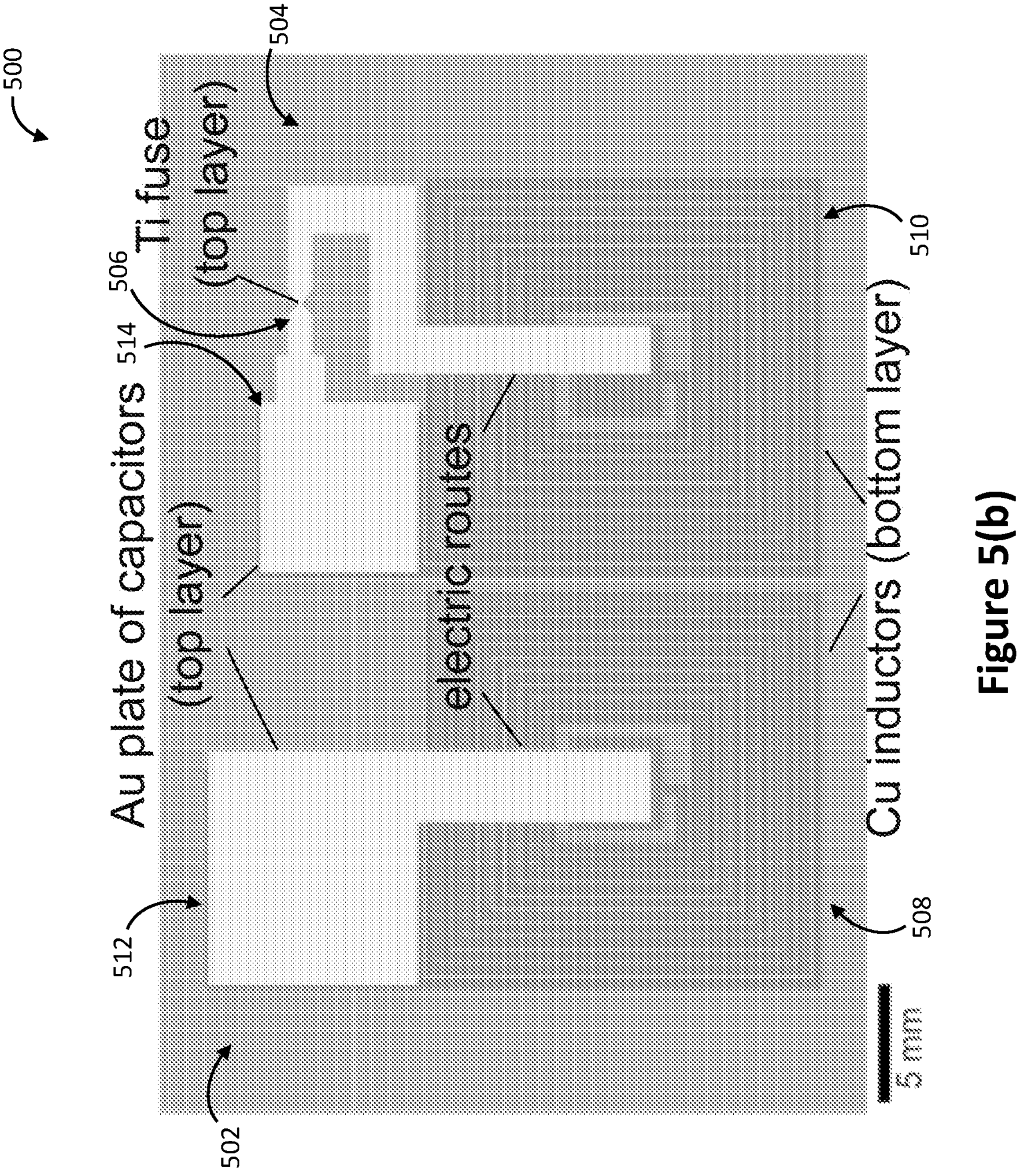

FIGS. 4(*a*)-4(*c*) depict schematic, perspective views of an interconnect or trace, as well as a structural fuse, of a strain sensor in accordance with one example.

FIG. 5(*a*) is a flow diagram of a method of manufacturing a strain sensor in accordance with one example.

FIG. 5(*b*) is a schematic, plan view of a strain sensor in accordance with one example.

Figure 6A:
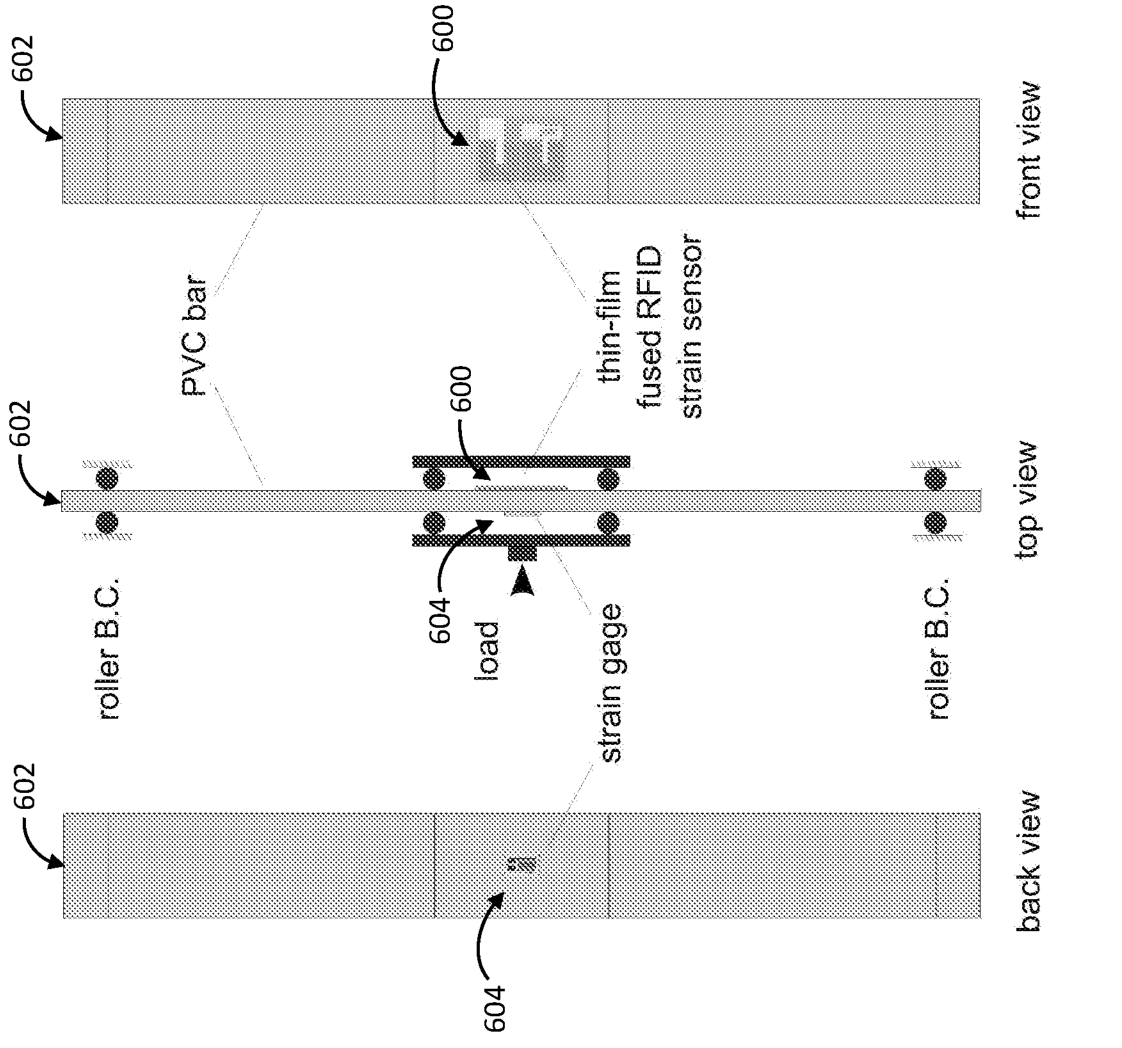
Figure 6B:
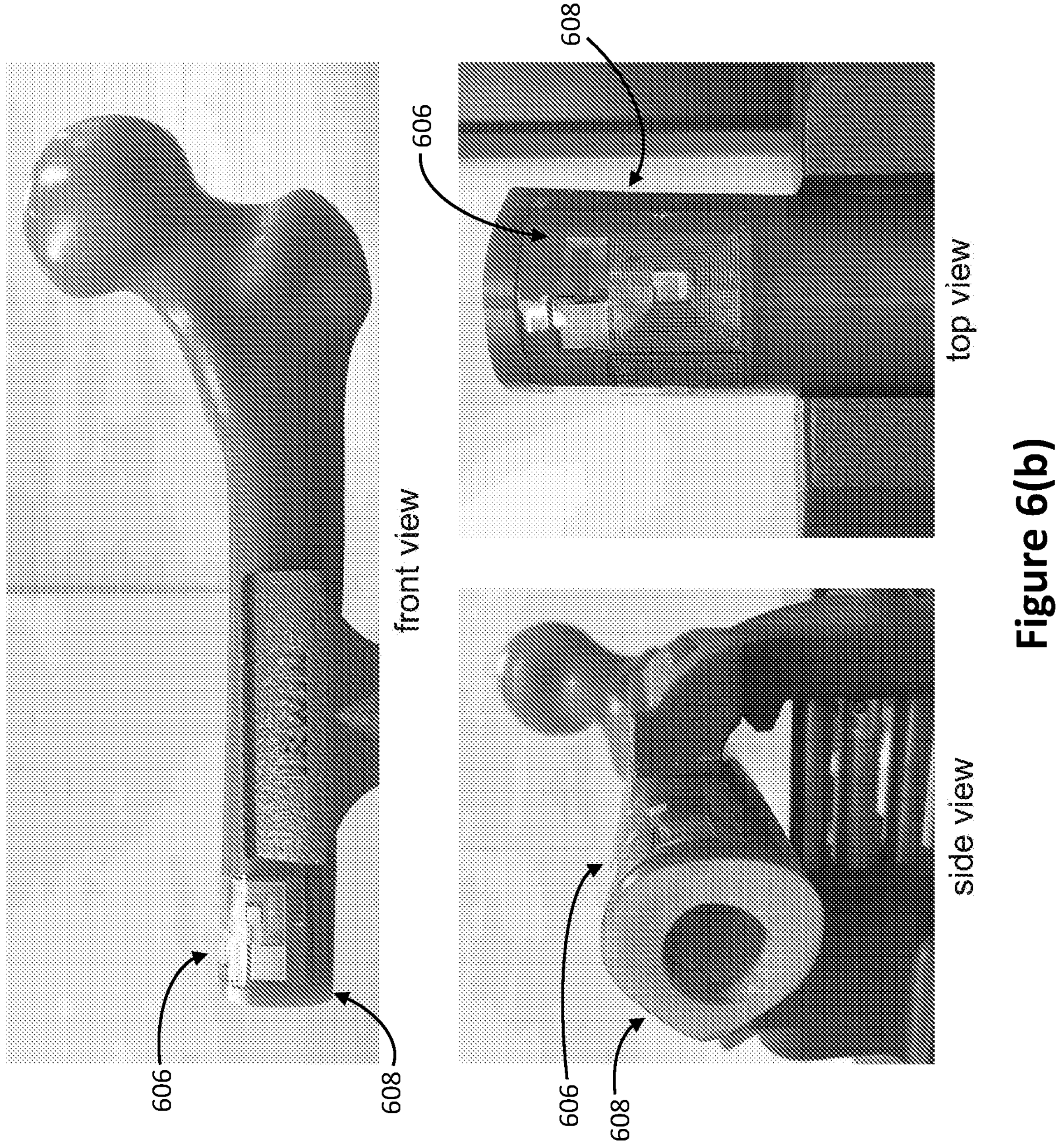

FIG. 6(*a*) is a schematic view of an apparatus for testing a strain sensor in accordance with one example.

FIG. 6(*b*) depicts perspective views of strain sensors applied to a bone in accordance with one example.

Figure 7:
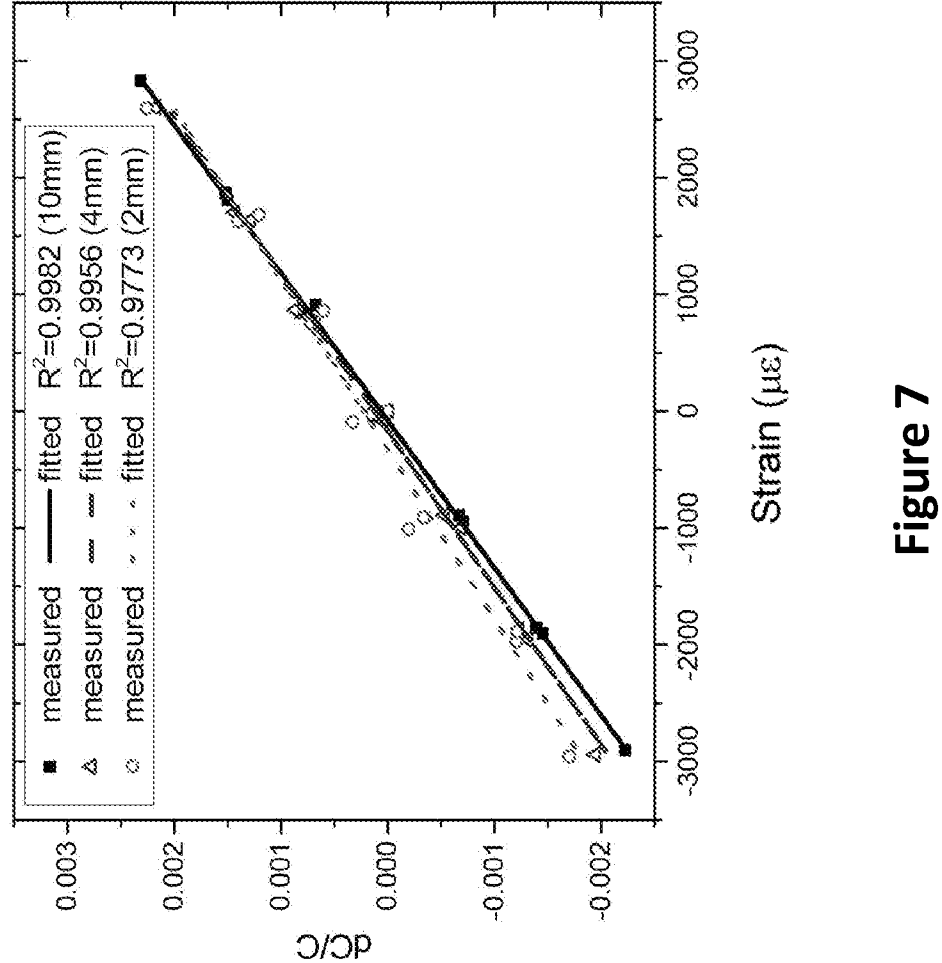

FIG. 7 is a plot of relative change of capacitance as a function of applied strain for three examples of strain sensors.

Figures 8A, 8B:
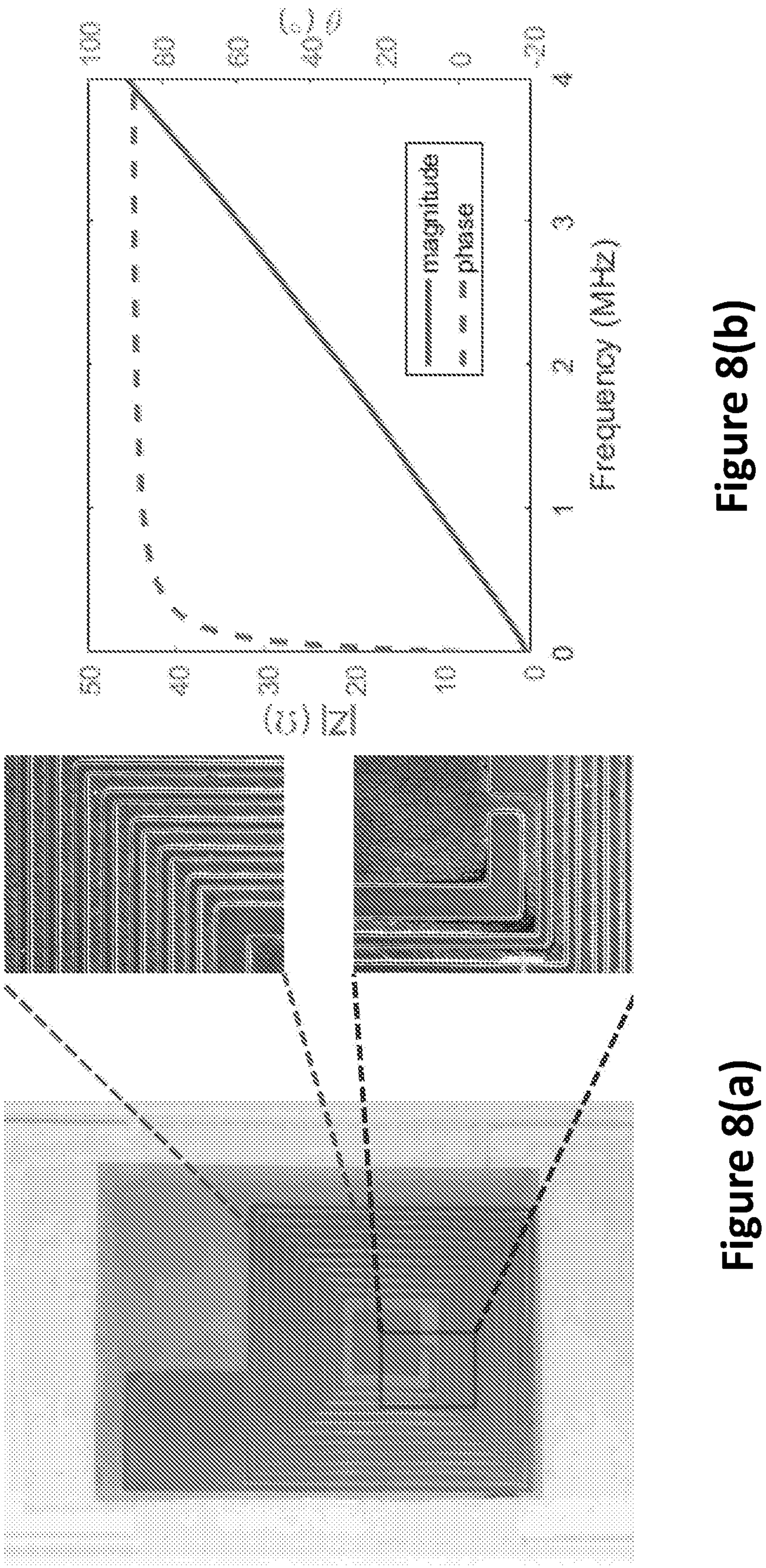

FIG. 8(*a*) depicts plan views of an inductor of a strain sensor in accordance with one example.

FIG. 8(*b*) is a plot of phase and impedance curves for a characterization of the inductor of FIG. 8(*a*).

Figure 9B:
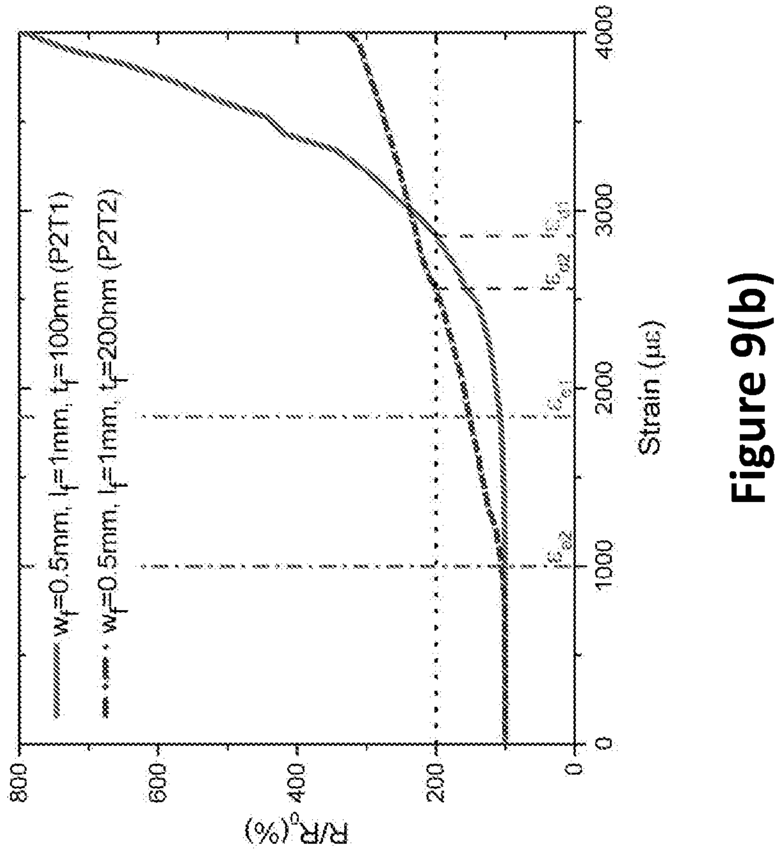
Figure 9A:
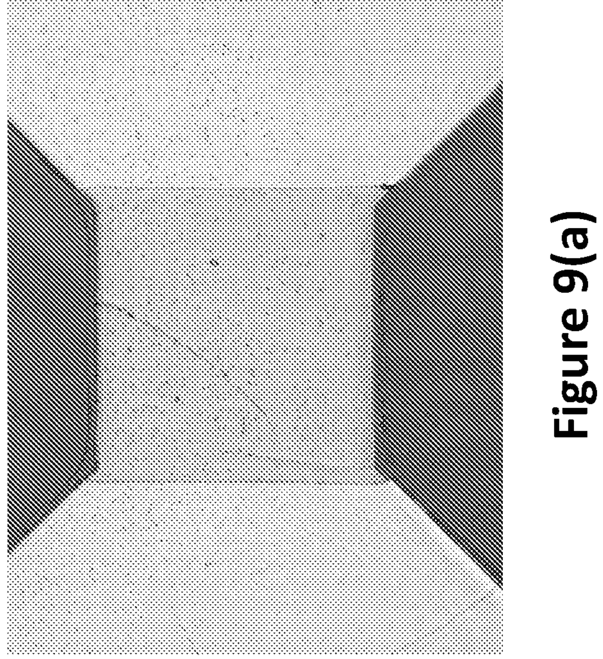

FIG. 9(*a*) depicts a plan view of a structural fuse of a strain sensor in accordance with one example.

FIG. 9(*b*) is a plot of resistance of the structural fuse of FIG. 9(*a*) as a function of tensile strain.

Figure 10B:
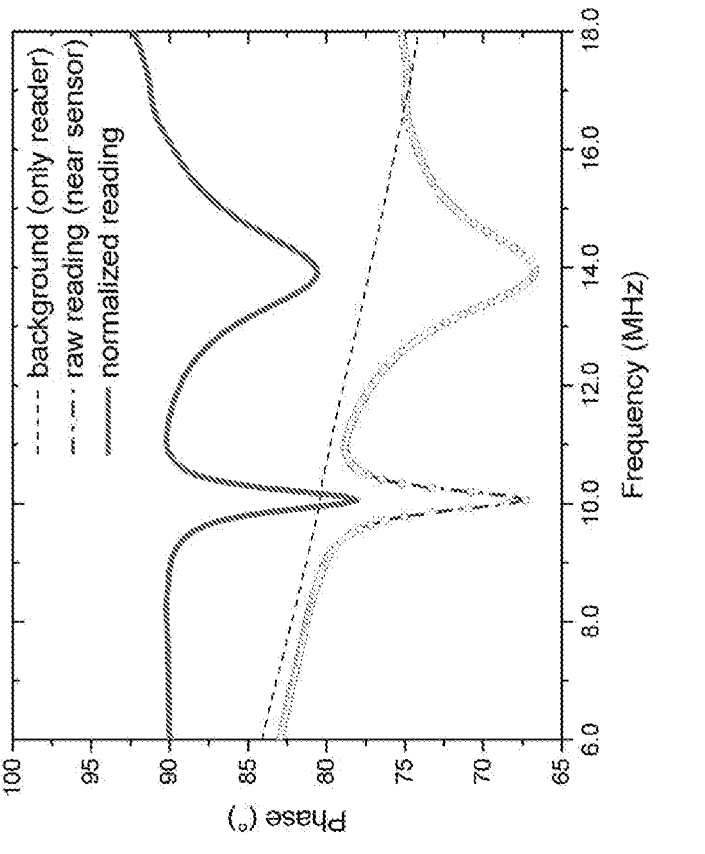
Figure 10A:
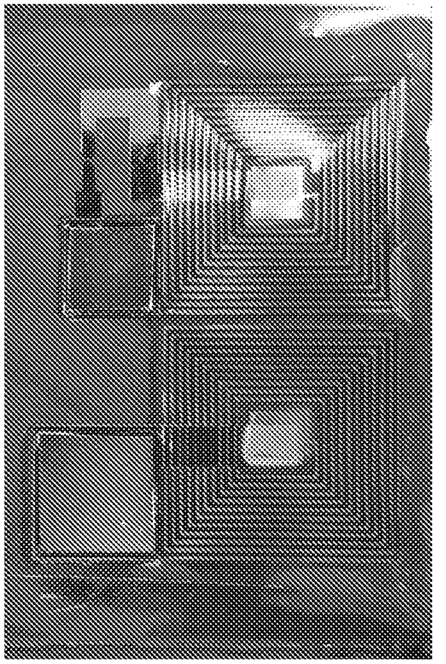

FIG. 10(*a*) depicts a plan view of a strain sensor device having two strain sensor circuits in accordance with one example.

FIG. 10(*b*) is a phase-frequency plot of a signal captured by an inductive reader near the strain sensor device of FIG. 10(*a*).

Figure 11:
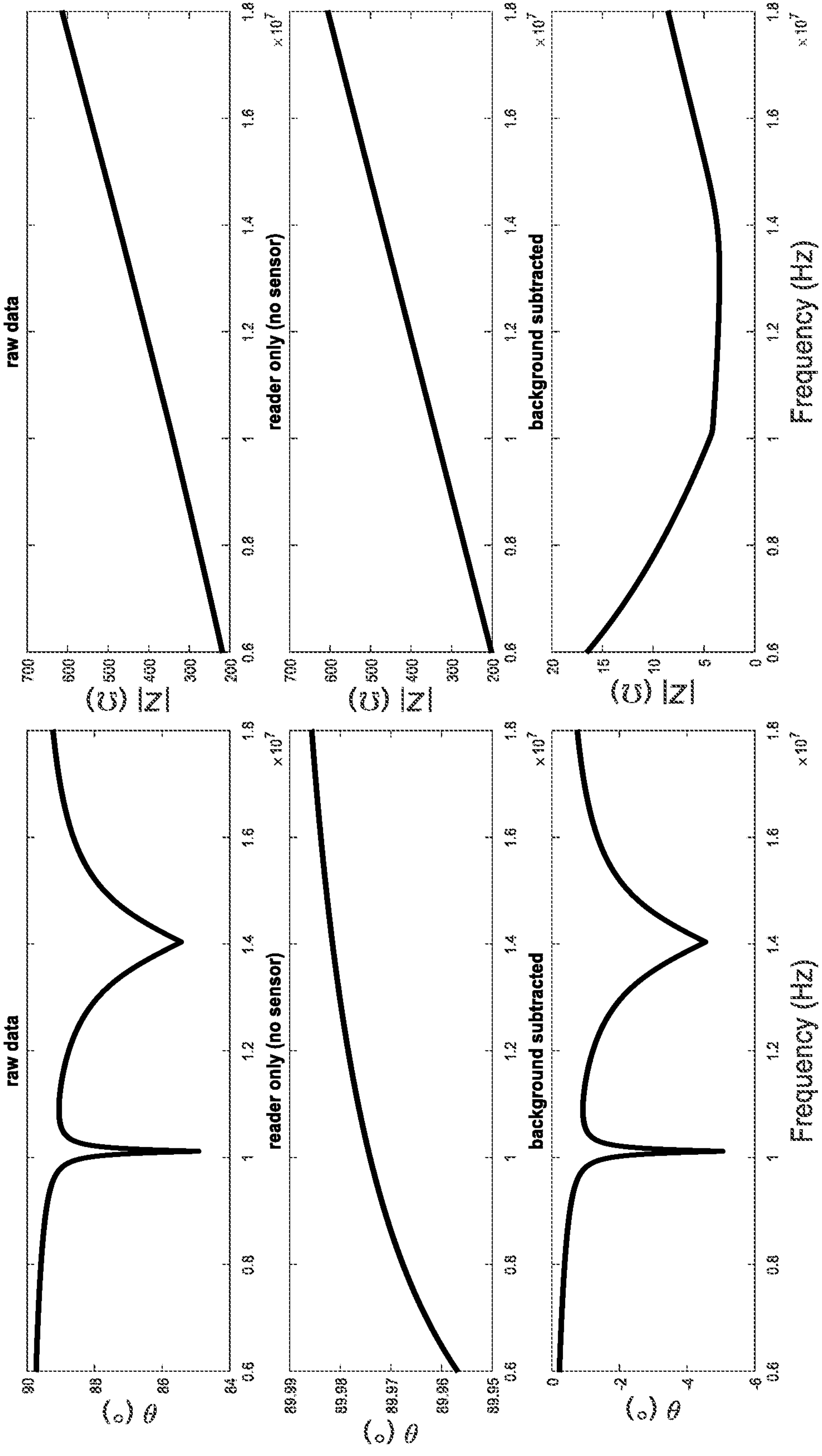

FIG. 11 are simulated impedance plots of phase and magnitude of response signals of a strain sensor-reader coupled system, the reader alone (without the strain sensor), and the strain sensor alone (by removing the reader impedance from the impedance of the coupled system).

Figures 12A, 12B, 12C, 12D:
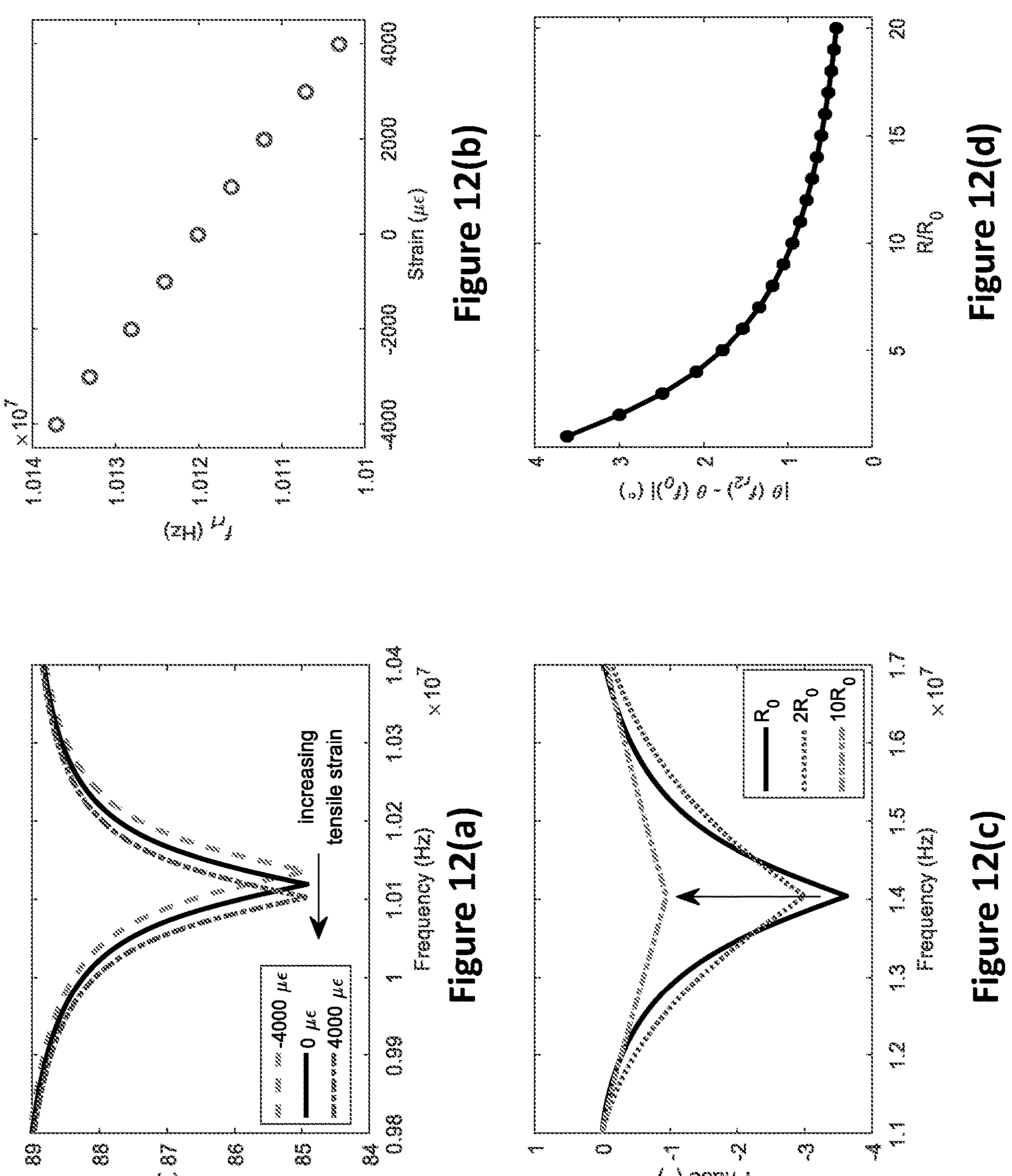

FIGS. 12(*a*)-12(*d*) are plots of responses of strain sensors in accordance with examples, including phase impedance plots under a number of different strain conditions (FIG. 12(*a*)), a plot of resonant frequency as a function of strain for a strain sensor in accordance with one example (FIG. 12(*b*)), a phase impedance plots normalized to a reference frequency (e.g., 11 MHz) (FIG. 12(*c*)), and a plot of the absolute phase difference between a second valley of a phase response and the reference point (FIG. 12(*d*)).

Figure 13B:
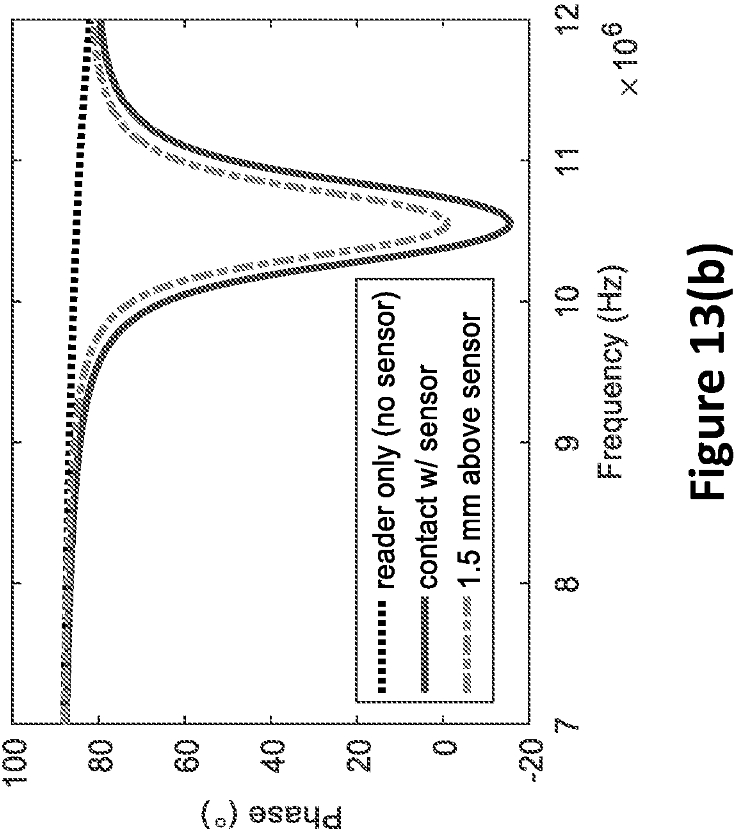
Figure 13A:
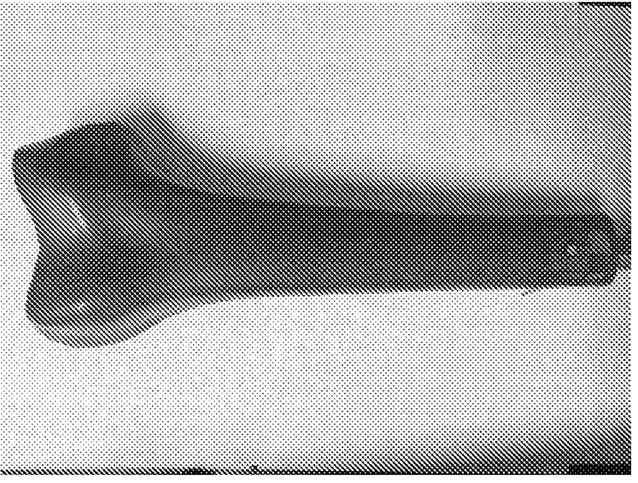

FIG. 13(*a*) is a perspective view of a thin film sensor applied to an end of a femur in accordance with one example.

FIG. 13(*b*) is a phase bode plot of the thin film sensor of FIG. 13(*a*) as measured by an inductive reader.

Figures 14A, 14B:
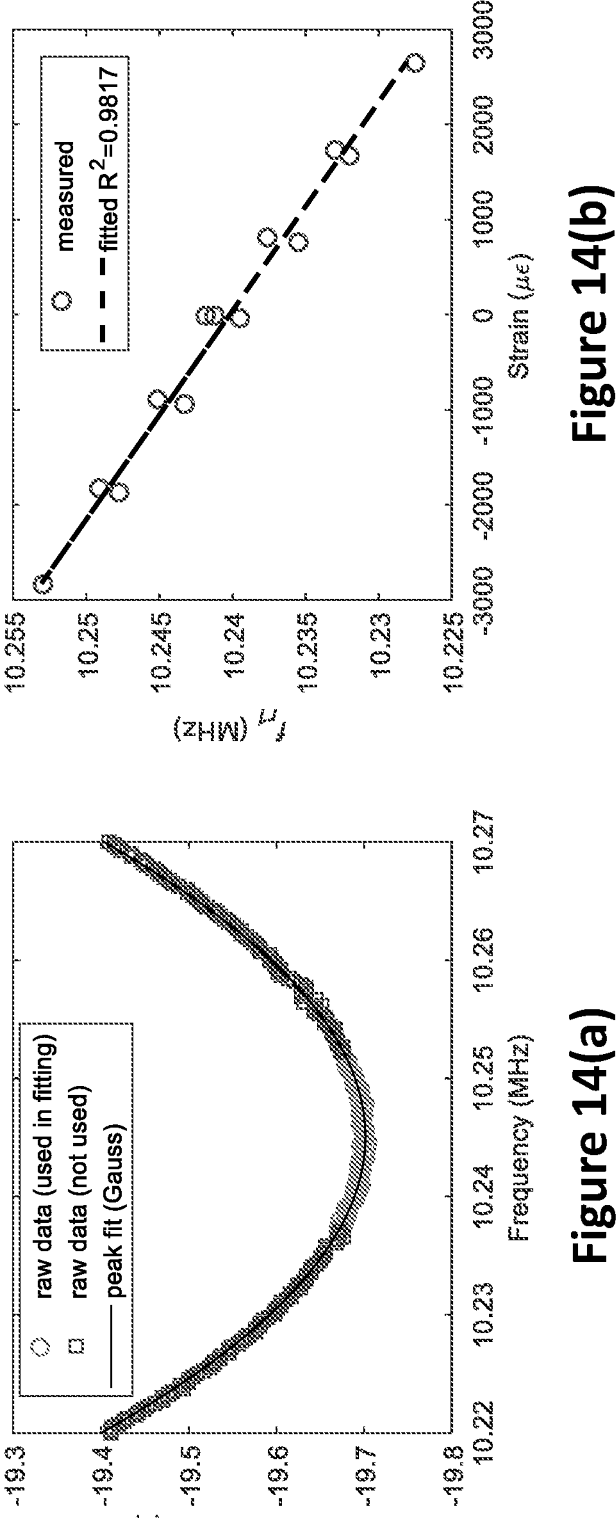
Figures 14C, 14D:
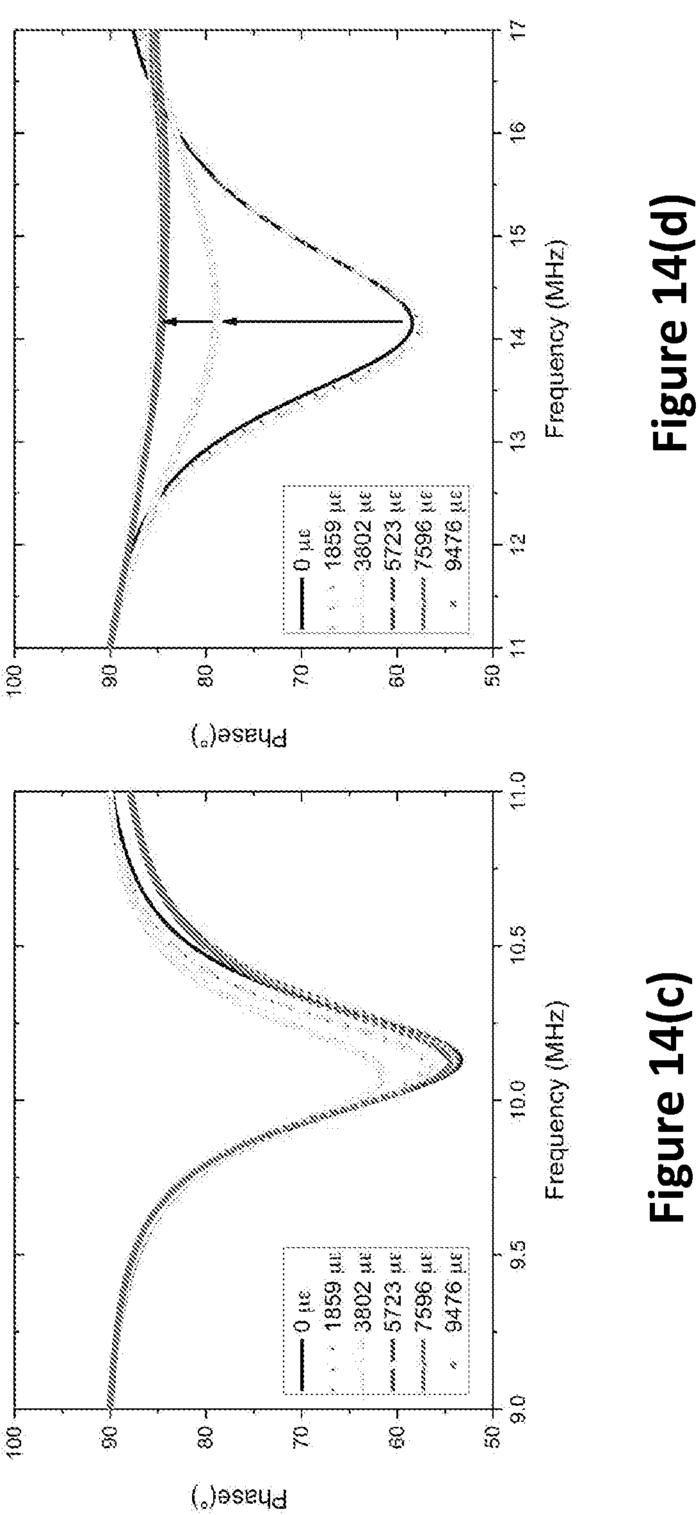
Figure 14E:
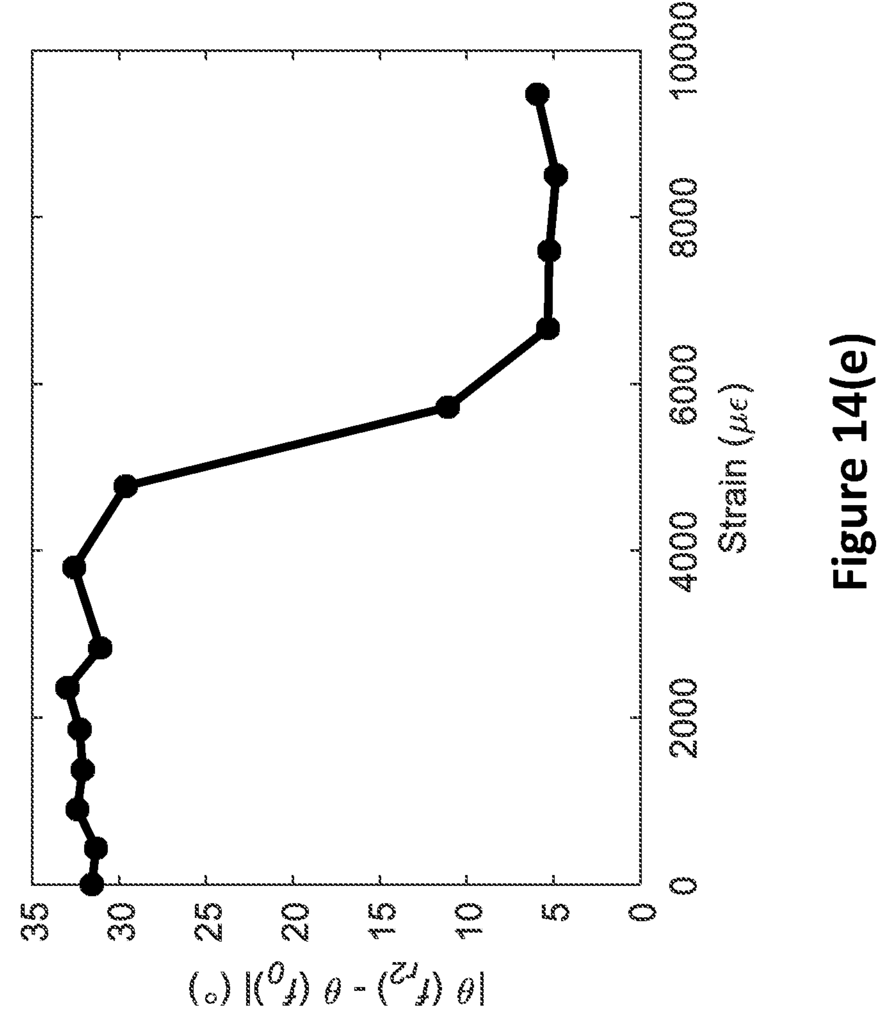

FIGS. 14(*a*)-14(*e*) are plots of (a) examples of gauss valley fitting near the resonant frequency of a first resistive-inductive-capacitive (RLC) circuit, (b) a response of the resonant frequency to the applied strain, (c) a first valley (normalized) in the phase response from the first RLC circuit, (d) a second valley (normalized) in the phase response from a second RLC circuit due to monotonically increasing tensile strain, and (e) the absolute phase difference between the second valley and a reference point versus monotonically increasing strain.

Figure 15:
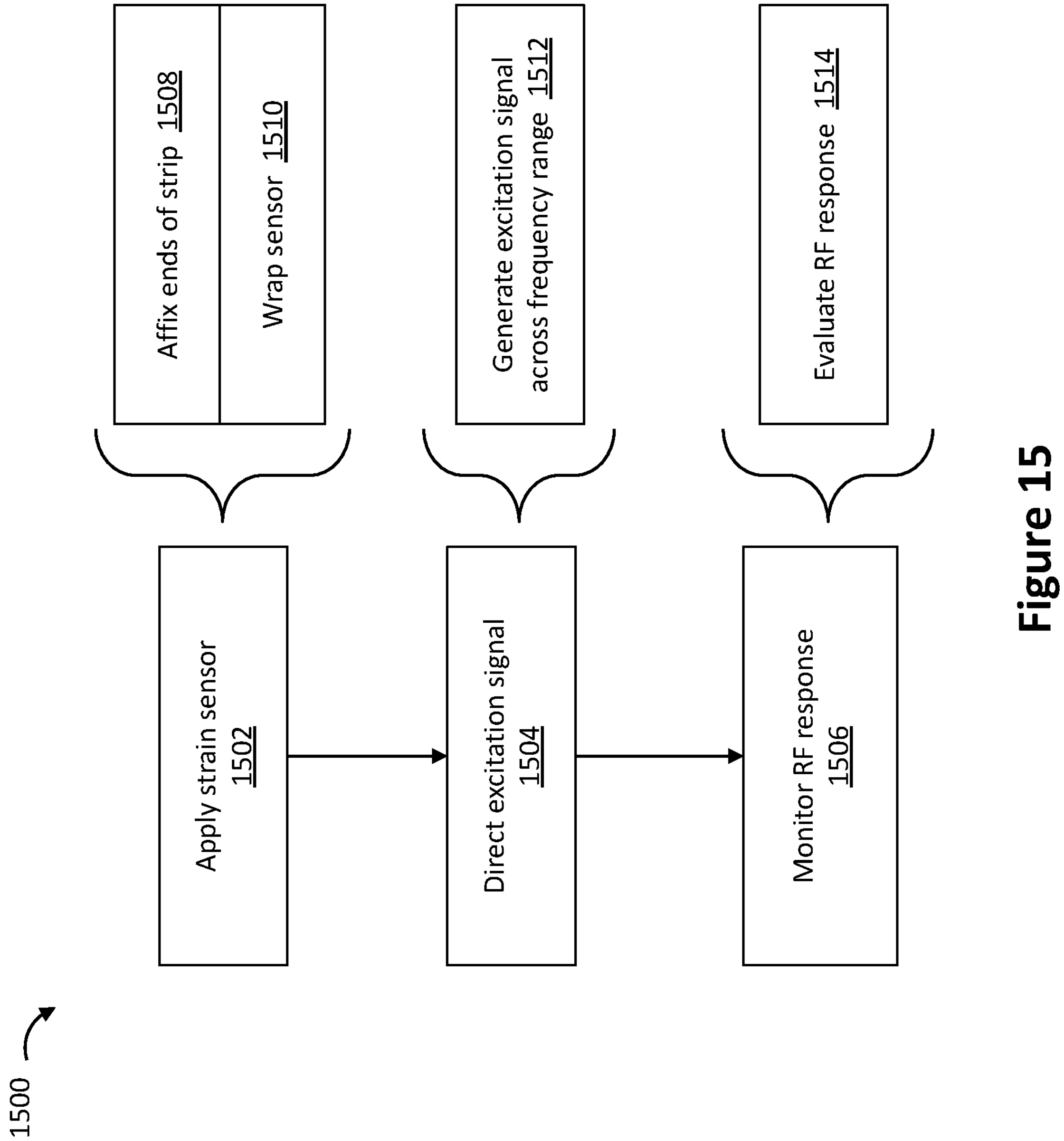

FIG. 15 is a flow diagram of a method of sensing hoop strain in an object in accordance with one example.

The embodiments of the disclosed devices, systems, and methods may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Devices, systems, and methods of sensing strain are described. Methods of manufacturing strain sensors are also described. The disclosed sensors are configured to measure tensile (e.g., hoop) strain. To that end, the disclosed sensors include a circuit in which a circuit trace has a non-uniformity that exhibits a nonlinear response under applied strain. The non-uniformity may be or include a resistive element of the trace that tears as the trace is subjected to tensile strain above a threshold. In this manner, the sensor may be used to track hoop strain associated with circumferential bone growth common in compress osseointegrated prosthesis fixtures. In some cases, the disclosed sensors may also include another circuit directed to measuring axial strain using a parallel plate capacitor, the capacitance of which changes under applied strain.

The strain sensors and circuit(s) thereof may be fabricated via thin film fabrication techniques and procedures, including, for instance, photolithographic and physical vapor deposition (PVD) procedures. The thin film fabrication techniques are used to deposit and pattern layers of one or more circuits on a flexible (e.g., polymeric) substrate. The layers may be bio-compatible polymers and metals In some cases, the strain sensors are composed of biocompatible materials. For instance, one or more of the deposited layers may be composed of biocompatible polymers (e.g., parylene) and metals (e.g., gold and titanium). The flexible substrate may also be composed of a biocompatible polymer.

The biocompatibility of the layers of the disclosed strain sensors render the sensors well suited for in vivo monitoring the growth and strain response of bone in osseointegrated prostheses, e.g., after implantation of a compress osseointegrated prosthesis. In vivo monitoring of bone growth at or near implants may offer insight to bone healing, osseointegration, and long-term implant performance. For example, the disclosed sensors and methods may be used to acquire quantitative data that can assess osseointegration after implantation and determine the condition of both bone and fixture over the life span of the prosthesis. With such biocompatibility, the disclosed sensors may be used to monitor the growth and strain response of bone.

The disclosed sensors may be configured as thin film sensors. The thin film nature of the disclosed sensors and the flexibility of the substrate may allow the sensors to conform or deform with an object or structure on which the sensors are installed. The disclosed sensors may thus have a high degree of versatility. The conformability of the disclosed sensors may be beneficial in connection with monitoring bone and implants where surfaces are curved and complex.

Although described in connection with bone growth monitoring, the disclosed strain sensors are useful in a wide variety of contexts and applications. The disclosed sensors are thus not limited to applications to bone. The disclosed sensors may instead be applied to various types of objects. For instance, the disclosed sensors may be used in various structural health monitoring contexts in which an object expands with corrosion or other deterioration. For example, the disclosed sensors may be applied to metal rods in bridges or other structures. Other example applications are crack detection and fatigue detection.

The circuit(s) of the disclosed sensor may be designed to be passive. Each circuit may be or include a resistive-inductive-capacitive (RLC) circuit. One of the circuits may include a resistive fuse element for peak strain detection, while another circuit includes a strain-sensitive parallel plate capacitor. The inductive elements of each circuit are used for wireless coupling with a wireless (e.g., inductive) reader or interrogator. In some cases, each inductive element is a spiral coil inductor. The wireless (e.g., inductive) coupling allows the reader to be positioned outside the body, while the sensor is attached to, for instance, the surface of the bone being monitored.

Figure 1A:
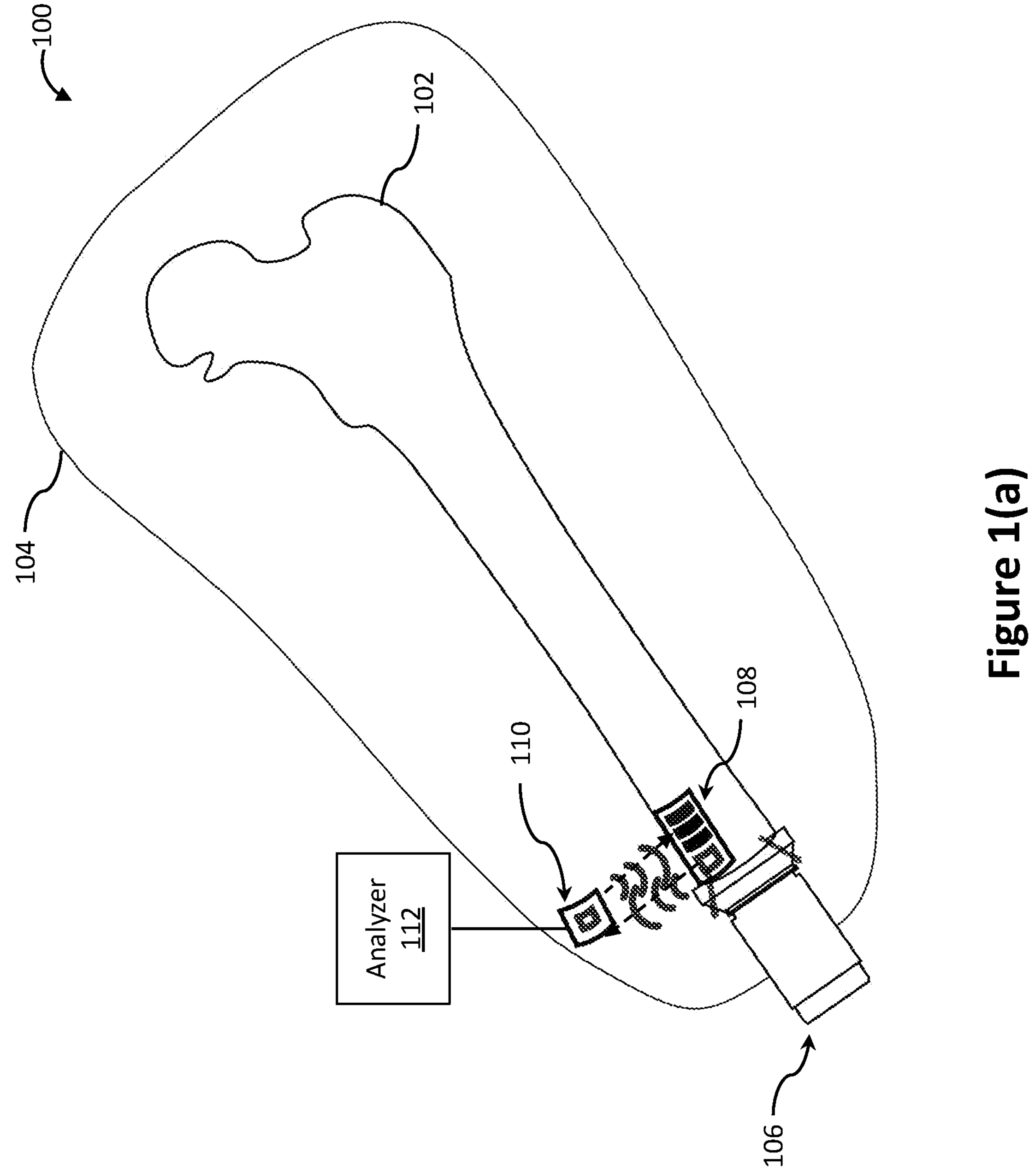
FIG. 1(*a*) is a schematic view of a strain sensing system configured in accordance with one example and directed to a bone monitoring application.
Figure 1B:
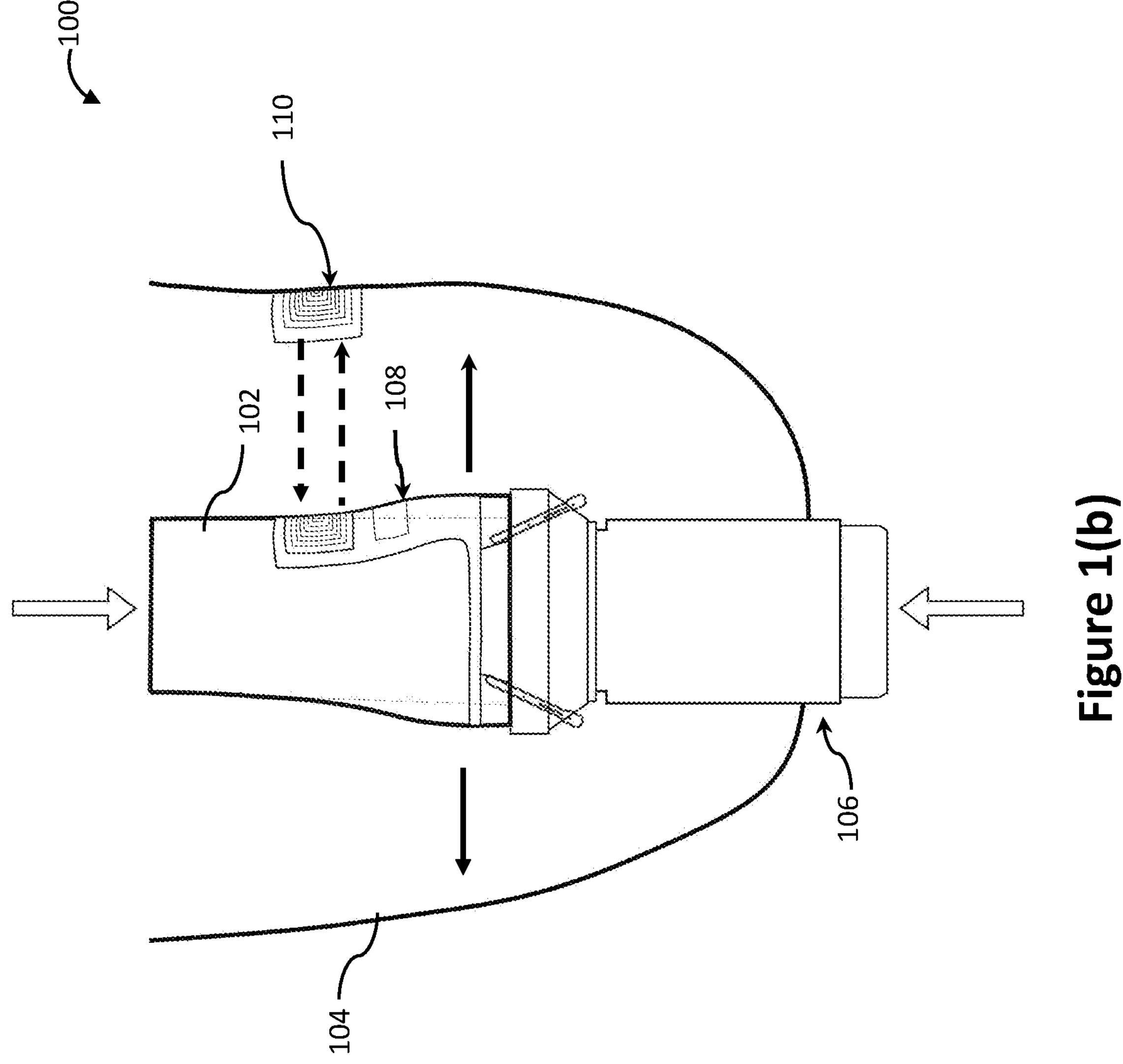
Figure 1C:
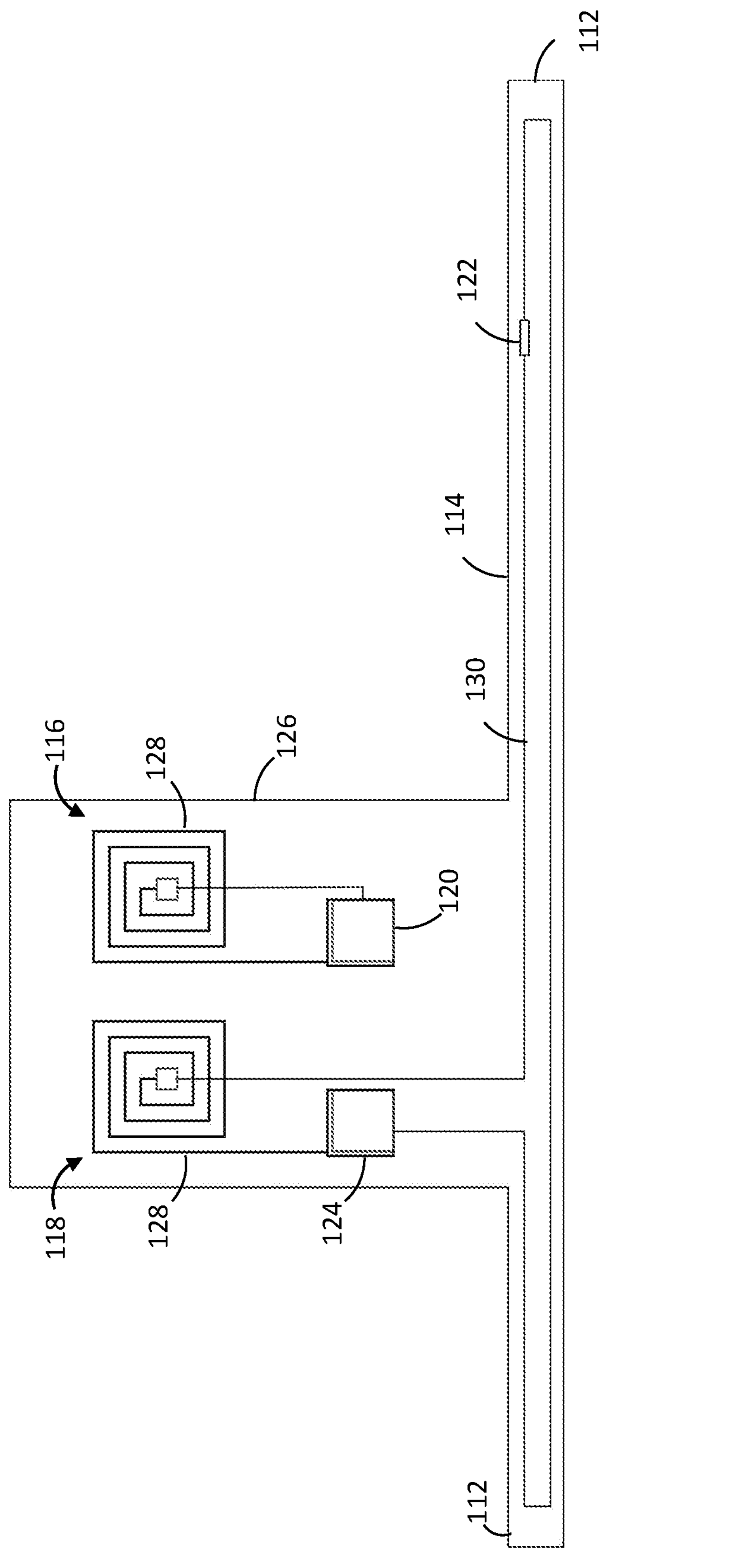

FIG. 1(*a*) depicts one example of a sensor system 100 to monitor growth and strain response of a bone 102 of a body 104 to which an osseointegrated prosthesis 106 has been applied. The sensor system 100 includes a biocompatible wireless thin-film sensor 108 (or sensor device) configured for use in compress-type osseointegrated prosthesis fixtures, but the sensor 108 is suitable for use in a broader set of orthopedic implant applications, as well as other applications, such as SHM applications. As described below, the sensor 108 includes one more circuits (e.g., RLC circuits) configured to be wirelessly coupled to an inductor 110 of the system 100. The inductor 110 is coupled to an impedance analyzer 112 of the system 100 positioned outside the body 104. The inductor 110 and the analyzer 112 may together be considered to be components of a reader or interrogator of the system 100.

The thin film sensor 108 is attached to the bone 102. In this example, the sensor 108 is wrapped around the periphery (e.g., circumference) of the bone 102, as also shown in FIG. 1(*b*). The sensor 108 may be applied during surgical implantation to the osseointegrated prosthesis. As shown in the example of FIG. 1(*c*), ends 112 of an elongated section 114 of the sensor 108 are sintered or otherwise attached to the bone 102. Other portions or sections of the sensor 108 may be unattached to the bone 102 and, thus, are capable of slippage relative to the bone 102 as the growth of the bone occurs. Still other portions or sections may be attached, including, for instance, portions directed to sensing axial strain.

As shown in FIG. 1(*c*), the sensor 108 may include two separate RLC circuits 116, 118. The circuit 116 is configured to measure axial strain (e.g., compressive and tensile) in the bone 102 (FIG. 1(*a*)) using a parallel plate capacitor 120 whose dielectric layer changes thickness due to planar strain. The circuit 118 includes a resistive element 122 (e.g., titanium resistive element) configured to track monotonically increasing hoop strain in the bone. The frequency responses of the two RLC circuits 116, 118 are tuned to different resonant frequencies to allow the single inductive reader 110 (FIG. 1(*a*)) connected to the impedance analyzer 112 (FIG. 1(*a*)) to measure the sensor output. A different resonant frequency may be established for the circuit 118 by including a capacitor 124 (e.g., parallel plate capacitor) that has a different capacitance than the capacitor 120. In other cases, the system 100 may include multiple analyzers. The different resonant frequencies allow the states of the resistive element 122 and the capacitor 120 to be ascertained via analyses of the respective responses of the two RLC circuits 116, 118 to an excitation signal received via the inductive coupling between the inductances of the circuits 116, 118 and the inductor 110 (FIG. 1). The excitation signal may be a radio frequency or other electromagnetic signal.

The capacitors 120, 124 and other components of the circuits 116, 118 are fabricated using thin film procedures and implantable materials. In this case, gold, titanium, and polyimide are used, but other biocompatible metals and polymers (e.g., parylene) may be used. The components of the circuits 116, 118 are sealed within a biocompatible coating (e.g., polyimide or parylene). The configuration and other characteristics of the capacitors 120, 124 may vary from the examples shown. For example, the capacitor 124 may be or include a parasitic capacitance.

The capacitor 120 may be configured as a square parallel plate capacitor. Other shapes may be used. In this example, the capacitor 120 may include two gold conductive layers sandwiching a polyimide dielectric layer fabricated upon a flexible substrate 126 (e.g., polyimide substrate). Gold and polyimide are biocompatible materials that are robust to harsh thermal, chemical, and physical environments. The planar dimensions of the capacitor 120 may vary, examples of which are addressed below.

The theoretical value of capacitance, C, for a parallel plate capacitor is, $$C = e_r e_0 \frac{A}{d} \tag{1}$$

where A is the area of overlap between the two plates (if the shape is rectangular, A=wl where w and l are width and length, respectively), $e_r$ is the relative static permittivity of the material between the plates (e.g., for polyimide $e_r$=3.4), $e_0$ is the electric constant ($e_0$=8.854×10−12 F·m$^{-1}$), and d is the distance between the plates. Derived from equation (1), the change in capacitance that is caused by changes in the geometry of the capacitor can be represented as:

$$\delta C = \varepsilon_r \varepsilon_0 \left( \frac{w \delta l}{d} + \frac{l \delta w}{d} - \frac{wl}{d^2} \delta d \right) \tag{2}$$

Hence, $$\delta C / C = \varepsilon_x + \varepsilon_y - \varepsilon_z \tag{3}$$

where $\varepsilon_x$, $\varepsilon_y$ and $\varepsilon_z$ correspond to strain along the length, width and thickness of the parallel plate capacitor, respectively. Under the assumption of plane stress ($\sigma_{zz}=\sigma_{zx}=\sigma_{zy}=0$), $\varepsilon_z$ can be computed as, $$\varepsilon_z = -\frac{v}{1-v}(\varepsilon_x + \varepsilon_y) \tag{4}$$

where v is the Poisson's ratio of the dielectric polymer situated between the conductive plates. By substituting equation (4) into equation (3), the relative change in capacitance for a free-standing capacitor under plane strain can be written as:

$$\delta C / C = \frac{1}{1-v}(\varepsilon_x + \varepsilon_y) \tag{5}$$

When the free standing capacitor is under perfect uniaxial tensile loading (e.g., $\sigma_x=0$ and $\sigma_y \neq 0$), then $$\frac{\delta C}{C} = \frac{1}{1-v}\varepsilon_y.$$

When the thin-film capacitor is affixed to a structure that is under uniaxial tensile load, then the Poisson's ratio of the structure (or substrate), $v_s$, is considered. In that case, the percent change in capacitance is $$\delta C / C = \frac{1}{1-v}(\varepsilon_x + \varepsilon_y).$$

Finally, the gage factor, $GF_c$, of the capacitive strain sensor can then be calculated as, $$GF_c = \frac{1-v_s}{1-v} \tag{6}$$

where $GF_c$ is defined as the percent change in capacitance per unit strain.

Figure 2:
FIG. 2 is a flow diagram of a method of manufacturing a strain sensor in accordance with one example.

A flow diagram of one example of the capacitor fabrication process is shown in steps a1-a6 of FIG. 2. The capacitor fabrication begins with the attachment (step a1) of a flexible substrate (e.g., 50 μm polyimide (PI) flexible substrate, such as the film commercially available as American Duarfilm FT Kapton 200 HN), to a silicon wafer using, e.g., quartz wax, such as Logitech 0CON-200. The silicon wafer is a rigid, sacrificial substrate used only during processing. Other sacrificial substrates may be used.

Once the flexible substrate is bonded to the sacrificial substrate, a layer of gold is patterned (step a2) on top of the flexible substrate to serve as both the bottom plate of the capacitor and electrical traces for the sensing circuit. The gold layer is deposited in a controlled manner using optical lithography. In this example, the polyimide substrate surface is treated with an oxygen plasma etch to promote the adhesion of metal layers upon it. Next, a sacrificial photoresist layer is spun on the substrate. Areas of the photoresist layer are exposed to UV light through a stencil-like mask. The photoresist layer is developed to remove areas of the layer that have been exposed to light with solution. Next, a thin metallic adhesion layer (e.g., a chromium layer having a thickness of about 50 nm) is deposited, followed by deposition of a conduction metal layer (e.g., a gold layer having a thickness of about 700 nm). Both layers may be deposited over the entire flexible substrate using physical vapor deposition (PVD). The photoresist remaining is exposed to lift off the undesired metal layer leaving only the desired pattern of metal, which is the bottom capacitor plate and electrical traces of the sensor.

After the initial conduction metal layer of gold is deposited, a dielectric layer (e.g., a polyimide layer, such as HD Microsystems PI 2525) is spin-coated (step a3) onto the flexible substrate, for instance, at a speed of 5000 rpm and is soft baked at 90° C. until firm. The polyimide layer may then be fully cured in a vacuum oven in a nitrogen gas environment by ramping from, e.g., 25° C. to 350° C., and holding for about one hour before gradually cooling back to 25° C. The thickness of polyimide layer spin-coated at 5000 rpm may be around 5.5 μm after curing for 30 min at 200° C. and 30 min at 350° C. Although curing occurs for one hour at 350° C., the thickness of the cured polyimide layer is confirmed to still be approximately 5.5 μm.

The polyimide layer is then etched (step a4) using reactive ion etching (RIE). Etching is intended to pattern the dielectric layer in the capacitor and to remove the polyimide covering the gold electrodes that are connected to the bottom plate of the capacitor. A layer of aluminum is first sputtered to the top surface of the polyimide layer to create a hard mask. Lithography and wet chemical etching is used to pattern the aluminum mask. With the hard mask in place, the substrate is placed in a chamber parallel plate tool (e.g., Plasmatherm 790) for RIE. The etch rate is controlled to ensure the 5.5 μm upper layer of the polyimide layer is removed except where masked by the aluminum layer.

Using the same procedure described for the lower gold plate, an upper gold plate (e.g., 700 nm thick) is deposited and patterned (step a5) on the polyimide dielectric layer using, for instance, a 5 nm chromium adhesion layer. Following the fabrication process, the polyimide substrate is lifted (step a6) from the silicon wafer.

As shown in FIG. 1(*c*), each circuit 116, 118 includes a respective inductor 128 for wireless communication. In this example, the inductor 128 of each circuit 116, 118 is similarly configured (e.g., dimensioned, number of turns, etc.). The circuits 116, 118 may thus have the same amount of inductance. In other cases, the inductance differs between the circuits 116, 118. Each inductor 128 includes an arrangement of traces disposed on the flexible substrate. In this case, each inductor 128 has a spiral coil arrangement. The configuration, construction, and other characteristics of the inductor 128 may vary from the example shown. For instance, the arrangement of the inductors 128 may not be disposed within a single layer as shown.

Figure 3:
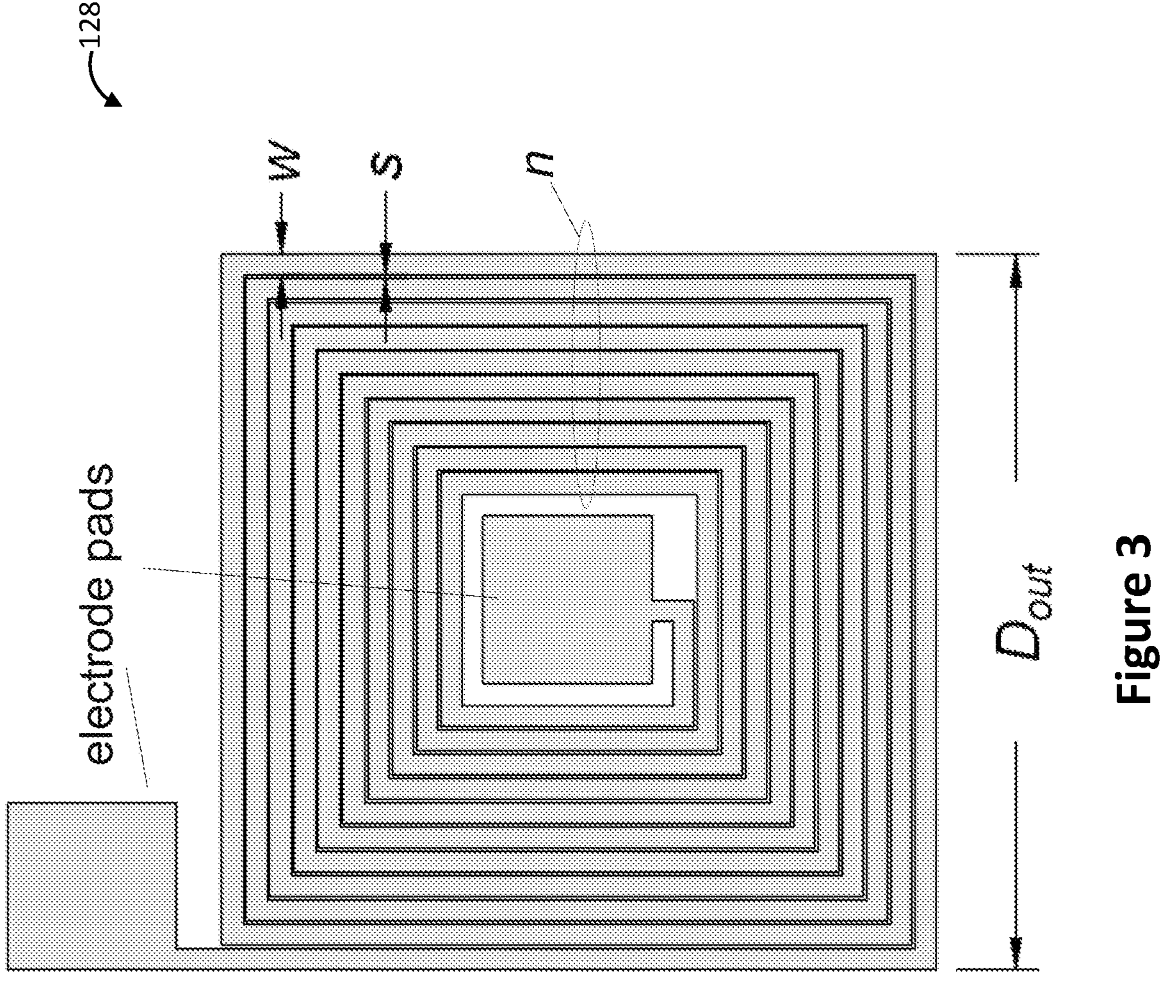
FIG. 3 is a schematic, plan view of an inductor of a strain sensor in accordance with one example.

FIG. 3 depicts one example of the inductor 128 in greater detail. Each inductor 128 may be optimized for inductive coupling of the sensor 108 with a reader, and also tailored to be insensitive to in-plane strain (e.g., $\varepsilon_x$, $\varepsilon_y$). In this case, the inductor 128 has a square layout, but other layouts or shapes may be used. The inductance of a square spiral inductor can be calculated from the inductor diameter ($D_{out}$), turn width (w), spacing between turns (s), and number of turns (n). The inductor 238 may be configured to maximize the coil inductance while simultaneously minimizing the resistance of the inductor 128, which means maximizing the quality factor, Q, as defined:

$$Q = \frac{\omega L}{r} \tag{7}$$

where L is the inductance, r is the DC resistance (DCR), and ω is the radian operating frequency. Geometry of the inductor 128 may play a role in connection with attempts to achieve a high quality factor. In this example, a single-layer, thin-film, square coil antenna is used to limit strain sensitivity and to maximize utilized geometry; the parameters n, s, and w may be optimized to maximize Q. The thickness of the thin film inductor 128 is useful in establishing the DC resistance in equation (7) with the optimized planar geometry. For example, a design of the inductor 128 is $D_{out}$=16.925 mm, w=500 μm, s=75 μm, and n=10, which yields a theoretical inductance of L=1.386 μH.

An example fabrication flow for the inductor 128 is shown in steps b1-b6 of FIG. 2. In order to achieve a high Q, the DC resistance (DCR) of the metal layer used to form the inductor 128 is minimized. In one example, the metal layer may be formed by electroplating gold and copper metal layers on PI. In other cases, a commercial polyimide substrate with a thick layer of copper cladding on both sides (e.g., DuPont Pyralux-AP9111R) may be used as the source of the conductive material and the flexible substrate, as shown in step b1 of FIG. 2. Starting with a substrate with copper (or other metal) cladding may be useful in achieving a uniform metal layer without stress issues that may otherwise cause brittle cracking in the metal layer. In one example, the three-layer film has a 25.4 μm thick polyimide layer sandwiched between two 35 μm thick layers of copper. Other thicknesses may be used. A layer of photoresist is patterned (step b2) as an etch stop, and the top copper layer is etched (step b3) to create the shape of the inductor. The bottom copper layer is etched (step b3) off completely at the same time. The photoresist is then stripped (step b4) from the inductor copper to fabricate a relatively thick copper film with a higher quality factor. The inductor is then encased (step b5) in a thick polyimide layer repeating the spin coating process previously described for the capacitor. Because a thicker polyimide layer is used to coat the inductor than is used as a dielectric layer for the capacitor, two layers of polyimide (e.g., HD Microsystems PI 2525) are spun and stacked over the inductor. The existing inductor and polyimide layers may be cleaned prior to spinning the initial polyimide encasing layer using an Argon plasma etch. Each layer of polyimide is spun at 2000 rpm for a target thickness of 13 μm. Each layer is soft baked at 90° C. until firm, and the final film is fully cured in a vacuum oven offering a nitrogen gas environment. In one example, the oven is ramped from 25° C. to 350° C. and holding at 350° C. for 1 hr before gradually cooling back to 25° C.

The inherent resistance R of the inductor 128 is used to establish the RLC circuit 116 (FIG. 1(*c*)). The inductor 128 and the capacitor 120 are connected with one another on the same substrate 126. In this example, the inductor 128 and the capacitor 120 are connected in series and in parallel. Other RLC circuit arrangements may be used. The RLC circuit 116 has a resonant peak at a frequency defined by the inductance, L, and capacitance, C, of the circuit 116. Changes in the capacitance due to strain may then result in a distinguishable shift in resonant frequency. In other cases, the RLC circuit 116 is used for purposes other than measuring axial or other strain. For instance, the RLC circuit 116 may be used for purposes of temperature compensation and/or other reference (e.g., to show that the sensor 108 and readout are functional).

In the example of FIG. 1(*c*), the RLC circuits 116, 118 of the sensor 108 are disposed on the same substrate 126. Further details regarding the configuration and fabrication of the RLC circuit 118 with the fuse 122 for threshold strain sensing are set forth below.

The circuit 118 includes an elongated trace 130 coupled to the inductor 128. The trace 130 may be or include a conductive loop disposed on the elongated section or strip 114 of the substrate 126 as shown. In other cases, the trace 130 may be a single line connected at ends of the elongated strip 114. The trace 130 is configured to bend longitudinally upon deformation of the flexible substrate 126. The bending or deformation of the flexible substrate 126 may be used to dispose the trace 130 along a curve such that the tensile strain to which the trace is subjected is a hoop strain.

To the extent that the substrate deformation also bends other components of the circuit 118, such as the inductor and/or capacitor, such components are configured such that the deformation does not modify the inductance or capacitance thereof (or at least not to a detectable extent). The radio frequency response of the circuit 118 is thus not affected by such bending of the other components.

The trace 130 includes a non-uniformity, which, in this example, is or includes the fuse 122. The fuse 122 is configured such that the trace 130 tears at the non-uniformity and exhibits a non-linear increase in resistance as a tensile strain to which the trace 130 is subjected reaches a strain threshold. The non-linear increase in resistance modifies a characteristic of the radio frequency response of the circuit. In some cases, the response characteristic is a phase of the response. Additional and/or alternative detectable response characteristics may be used in other cases, including, for instance, magnitude.

The circuit 118 includes the resistive fuse element 122 to detect high levels of strain, such as the hoop strain associated with circumferential bone growth. The fuse 122 may be considered a structural fuse, as the fuse 122 tears as the fuse 122 yields to tensile strain. The fuse 122 may be configured to have minimal but effectively constant electrical resistance until a strain threshold is reached, at which point the metal in the fuse yields. In some cases, the resistance of the fuse 122 exponentially increases after yielding under monotonically increasing levels of strain after yielding.

The fuse 122 may be or include a metal thin film. A metal thin film may be useful as the fused element because a metal layer can be easily fabricated using the thin film fabrication methods described herein. The fuse 122 may thus, in some cases, be formed as an integral part of the elongated trace 130. In some cases, titanium is selected as the fuse material because titanium has low resistance (pre-yield) and is less ductile compared to many other metals (such as gold). Another reason is that titanium may also be used as an adhesion layer of the trace 130, making both circuit design and fabrication more efficient and convenient.

In the example of FIGS. 4(*a*)-4(*c*), the trace 130 and the fuse 122 are fabricated as a lithographically patterned metal interconnect. The trace 130 may include a stack of metal layers, including, for instance, an adhesion layer and a conduction layer. In the example shown, the adhesion layer is or includes titanium and the conduction layer is or includes gold. Alternative, fewer, and/or additional metal layers may be used.

As shown in FIG. 4(*b*), the fuse 122 is formed via a necked-down, or thinned, section of the trace 130. In some cases, the necked-down section is formed by etching or otherwise removing some or all of the conduction layer (e.g., gold). Removal of the conduction layer may expose a small area of the underlying adhesion layer (e.g., titanium). The process is controlled to yield a titanium fuse element with length $l_f$, width $w_f$, and thickness $t_f$, as shown in FIG. 4(*c*).

The non-uniformity thus involves both a non-uniform composition of the trace, as well as a non-uniform thickness of the trace. The configuration, composition, and other characteristics of the non-uniformity in the trace may vary. For instance, the non-uniformity may involve only composition or only thickness in other cases. In still other cases, additional or alternative types of non-uniformities may be used. For instance, other dimensions or characteristics of the trace may be varied. For example, the integrity of the trace may be impacted in a manner that promotes tearing or other changes in resistance.

An example fabrication process for the metal fuse 122 is shown in steps c1-c6 of FIG. 2. First, the PI substrate is bonded (step c1) to the silicon wafer. The PI substrate has a titanium seed layer deposited (step c2) thereon based on the optical lithography and PVD steps previously described for forming the gold electrodes of the capacitor. In some cases, during metal deposition, the thickness of the titanium layer (which normally serves as a thin adhesion layer) may be enlarged to establish a lower initial resistance for the fuse 122. A photoresist mask is spun (step c3) on top of the gold layer and cured as an etch stop so that the gold can be etched (step c4) from only the fuse portion of the metal interconnect. The fabrication process is finished by removing (step c5) the photoresist and lifting (step c6) the film from the wafer.

The fabrication process shown in FIG. 2 may be sequentially implemented so that the components of the circuits 116, 118 may be formed on a common substrate, e.g., the flexible substrate 126 (FIG. 1(*c*)). For example, the sequence of steps b1-b6 may be implemented first, followed by steps c1-c6, and then followed by steps a1-a6. The order may differ in other cases. For instance, steps a1-a6 may be implemented before steps c1-c6. In some cases, one or more steps may be shared by the step sequences. For example, step a1 and step c1 may be implemented concurrently. Alternatively or additionally, steps a2 and c2 may be implemented concurrently.

An example process flow that integrates the fabrication of both sensor circuits on the same flexible substrate is shown in FIG. 5(*a*). The process flow is configured such that the electrical components of the two circuits, including two capacitors, two inductors and a fuse, are integrated to create a passive, wireless, thin film (or planar) strain sensor or sensor device 500, an example of which is shown in FIG. 5(*b*). The sensor device 500 includes two circuits 502, 504. The circuit 502 is configured to measure bone strain (using a capacitor and an inductor as described herein). The circuit 504 includes a resistive fuse 506 to detect high hoop strain in the bone (also using a capacitor and an inductor as described herein). The resistive fuse may be or include a titanium fuse, e.g., as described above. Each circuit 502, 504 has an inductor 508, 510 and a capacitor 512, 514 so that a read inductor can be used to interrogate the resonance of the circuit 502, 504. The resonant frequency of the circuit 502, $f_{r1}$, may be used as a reference to show that the sensor device 500 and readout is functional. Additionally, the frequency $f_{r1}$ may be utilized for strain sensing by monitoring the shift of $f_{r1}$ due to the strain-induced change in the capacitance of the strain sensitive capacitor. In the circuit 504, the fuse is configured to yield to detect when hoop strain exceeds a specific threshold. While the sensor device 500 may be applied to various orthopedic applications, the sensor device 500 may be optimized for monitoring bone-growth in osseointegrated prosthetics.

The sensor device 500 is fabricated via the following steps of the method shown in FIG. 5(*a*): (step a1) a polyimide film with copper claddings on one side is bonded to a silicon wafer; (step a2) the top copper layer is etched to create an inductor and the bottom layer of a capacitor on one side of the film (note, the bottom gold layer of the capacitor is replaced with copper); (step a3) the copper layer is encased in polyimide using spin coating and curing; (step a4) the polyimide layer is then etched using RIE to create a thin dielectric layer for the capacitors and to provide a route to connect the center of the inductor to the top parallel plate of the capacitor; (step a5) the top layer of the capacitor as well as an electrode connecting the top layer to the center of the inductor is patterned over the previous layers using optical lithography and a gold metal layer; (step a6) the gold at the fuse area is etched to expose the titanium seed layer as a fuse. The photoresist is then stripped to complete the fabrication process. In some cases, a final encasing polyimide layer is deposited over the final metal layer, e.g., for robustness and biocompatibility so that the sensor may be used in a medical environment.

It should be noted that the configuration and fabrication of the capacitors, when integrated into the sensor device 500, differs from the configuration and fabrication described above in connection with the capacitor component design. First, the bottom electrode is copper. This change in metal may not affect the capacitor performance because it is the dielectric layer that controls its performance. In step a3 of the method of FIG. 5(*a*), the copper layer of the inductor and lower electrodes of the capacitors are firstly encased by using two stacking polymer layers (e.g., about 13 μm thick polyimide). In order to fabricate the dielectric layer of the capacitors in a conservative fashion, the resulting polymer film (e.g., about 26 μm thick polyimide) is further etched, e.g., using RIE, in step a4 to form a dielectric layer (e.g., thickness of about 10 μm), rather than, for instance, directly spinning polyimide (e.g., about 5.5 μm thick). Hence, in a fabricated sensing device, the dielectric layer may be larger, thereby reducing the capacitance of the capacitors. While the capacitors may have lower levels of capacitance, the change makes fabrication of the fully integrated thin film sensing system easier.

Examples of the sensor devices were electrically characterized using an impedance analyzer (e.g., an Agilent 4294A) with impedance observed using phase (θ) and magnitude (|Z|) frequency sweeps. The resistance of the fuse components was measured using a digital multimeter (e.g., an Agilent 34461A).

To experimentally validate the thin film sensor (and its components), a sensor device 600 was tested on a standard PVC bar or coupon 602, as shown in FIG. 6(*a*), and on a synthetic sawbone, as shown in FIG. 6(*b*). First, the backside of the flexible polyimide films are roughed with sand paper and cleaned by acetone after liftoff from the rigid silicon substrate to promote better attachment to the testing coupons. The thin-film components may be bonded to the PVC coupon 602 using cyanoacrylate fast-acting adhesive (e.g., Tokyo Sokki Kenkyujo CN adhesive). A strain gage 604 was bonded to the back side of the same PVC coupon 602 to serve as a baseline measurement of strain. The PVC coupons 602 are then loaded in four point bending as shown in FIG. 6(*a*). A computer-controlled stepper motor is utilized to drive a turn screw linear actuator that applies load to a custom sample fixture.

Additional testing was performed on wireless strain sensors 606 with the thin films attached to a realistic bone surface 608. FIG. 6(*b*) shows the photos of a polyurethane femur model (i.e., sawbone) with the conformable thin-film strain sensor 606 bonded by cyanoacrylate fast-acting adhesive.

The testing provided the following results in connection with characterizing examples of the capacitor components. Three square capacitors with a various side lengths (2 mm, 4 mm and 10 mm) were first fabricated on polyimide using the process described above. The theoretical values of capacitance for the capacitors in addition to their gage factors are obtained using equation (1) and equation (6). The fabricated capacitors were mounted to the PVC coupons 602 and tested under four point bending with the impedance analyzer used to continuously measure impedance over a wide range of frequencies.

Experimental data was gathered to measure capacitance and to ascertain the capacitor gage factor. The details of the samples and the measured values of capacitances are shown in Table 1. The theoretical capacitances are all higher by roughly 3%. The lower measured capacitance of the thin film samples is attributed to slightly thicker dielectric layers than theoretically predicted (5.5 μm) by the process parameters.

TABLE 1

| Capacitance and gage factors of the fabricated capacitive strain sensors | | | | | | |
|---|---|---|---|---|---|---|
| | w or l | d | Capacitance (pF) | | Gage factor | |
| Sample | (mm) | (μm) | theoretical | measured | theoretical | measured |
| capacitor 1 | 2 | 5.5 | 21.89 | 21.11 | 0.83 | 0.69 |
| capacitor 2 | 4 | 5.5 | 87.57 | 85.18 | 0.83 | 0.74 |
| capacitor 3 | 10 | 5.5 | 547.34 | 529.44 | 0.83 | 0.79 |

Under four point bending, the gage factor may be estimated for the three capacitor samples. The change in capacitance as a function of strain was measured. The response of the relative change in capacitance for the three samples are plotted against measured strain in FIG. 7. The 4 and 10 mm sized capacitors are nearly linear with R-squared values near 1. The smaller 2 mm square capacitor is less linear but the R-squared values of a linear regression is still high at 0.98. Based on the dimensions of the capacitors listed in Table 1, the theoretical values of the gage factor may be calculated for the three thin-film capacitors. Because v is 0.34 for polyimide and $v_s$ is 0.45 for PVC at room temperature, the theoretical values of $GF_c$ of the capacitors is estimated to be 0.83 by using equation (6). The gage factors for the larger capacitors appear to converge toward the theoretical value. For example, the 10 mm capacitor is within 5% of the theoretical gage factor. These results indicate the accuracy and quality of the design and fabrication of the capacitors.

The testing provided the following results in connection with characterizing the inductor components. Five types of inductors with different geometric parameters were fabricated and tested as summarized in Table 2. The measured inductances were very close to the theoretical values, except for type 2, which had a smaller number of turns (n=4). A final fabricated thin-film copper inductor of type 3 is shown in FIG. 8(*a*) with the impedance magnitude and phase plotted as a function of frequency in FIG. 8(*b*). The final design was chosen to maximize the inductor quality factor, while minimizing the inductor footprint. The type 3 inductor, with Dout=16.925 mm, w=500 μm, s=75 μm, and n=10, was chosen as the inductor in the integrated device to achieve a balance between a large L/R value and a suitable size. The designed type 3 inductor with a footprint of roughly 17 $mm^2$ had its DCR measured as 934 mΩ. The inductance was estimated to be 1.691 μH with a quality factor of around 11.38 at 1 MHz, as determined from the impedance spectra.

TABLE 2

| Inductuctances and resistances of the fabricated thin-film inductors. | | | | | | | | |
|---|---|---|---|---|---|---|---|---|
| | Geometric parameters | | | | R (Ω) | L (μH) | | L/R (μH/Ω) |
| Type | $D_{out}$(mm) | w(μm) | s(μm) | n | meas. | theo. | meas. | meas. |
| 1 | 11.675 | 250 | 75 | 10 | 1.945 | 1.233 | 1.264 | 0.650 |
| 2 | 13.450 | 1000 | 75 | 4 | 0.455 | 0.192 | 0.426 | 0.937 |
| 3 | 16.925 | 500 | 75 | 10 | 0.934 | 1.386 | 1.691 | 1.810 |
| 4 | 19.900 | 1000 | 75 | 7 | 0.620 | 0.678 | 0.721 | 1.162 |
| 5 | 25.800 | 1000 | 75 | 11 | 0.702 | 2.035 | 2.133 | 3.038 |

The testing provided the following results in connection with characterizing the structural fuse. The fuse may be configured such that the evaporation process of the PVD-based fabrication, which may lead to stress states within the fabricated metal films, does not undesirably affect performance. An Angstrom Engineering EvoVac Evaporator was used to deposit the thin titanium layer during fabrication. Titanium resistive elements of varying geometries were fabricated. An example of one such fuse is shown under an optical microscope in FIG. 9(*a*) with $w_f$=0.1 mm, $l_f$=0.1 mm, and $t_f$=200 nm. The titanium elements were tested under monotonically increasing tensile strain using PVC coupons loaded in four-point bending (as previously described) with element resistance measured.

FIG. 9(*b*) shows two resistance responses to increasing tensile strain for specimens of varying film thickness (i.e., 100 and 200 nm). While there is some variation between the tests, the fuse resistances were insensitive to strain within the range of (0, $\varepsilon_e$) which corresponds to pre-yield stress in the titanium film. After yielding, the element resistance increased nonlinearly in a relatively exponential fashion. The resistance nonlinearity occurs due to the film undergoing plastic deformation while also forming micro-cracks due to high level of tensile strain at impurities in the film. A designed strain threshold is established by a resistance level that is two times the initial resistance ($2R_0$) as denoted as $\varepsilon_d$ or $\varepsilon_{2R0}$. Similarly, the strain when ten times and twenty times of the initial resistance were reached are denoted as $\varepsilon_{10R0}$ and $\varepsilon_{20R0}$, respectively.

The dimensions and labeling convention of the fuse samples with varying widths, lengths, and thicknesses are shown in Table 3. Five planar types (denoted P1 through P5) are categorized with the combination of three length options ($l_f$=0.1, 1 or 2 mm) and three width options ($w_f$=0.1, 0.5 or 1 mm). Three thickness types (denoted T1 through T3) have three thicknesses ($t_f$=100, 200 or 300 nm). Strain levels ($\varepsilon_{2R0}$, $\varepsilon_{10R0}$ and $\varepsilon_{20R0}$) corresponding to the resistances of $2R_0$, $10R_0$ and $20R_0$ for each fuse sensor in the P2 family are listed in Table 4. Both thinner (100 nm) and thicker (300 nm) titanium layers are more prone to large resistance increases. This result may be due to mechanical weakness in the film, resulting in lack of overall material in the 100 nm film, and greater residual stresses from deposition in the 300 nm film. As a result, the empirical evidence suggests the 200 nm film (i.e., T2) is a potentially more robust middle ground thickness.

TABLE 3

| Dimensions and labeling convention of fuse samples | | | | | |
|---|---|---|---|---|---|
| Sample | Planar type | | | Thickness type | |
| label | label | $l_f$ (mm) | $w_f$ (mm) | label | $t_f$ (nm) |
| P1T2 | P1 | 0.1 | 0.5 | T2 | 200 |
| P2T2 | P2 | 1 | 0.5 | T2 | 200 |
| P3T2 | P3 | 2 | 0.5 | T2 | 200 |
| P4T2 | P4 | 1 | 0.1 | T2 | 200 |
| P5T2 | P5 | 1 | 1 | T2 | 200 |
| P2T1 | P2 | 1 | 0.5 | T1 | 100 |
| P2T3 | P2 | 1 | 0.5 | T3 | 300 |

TABLE 4

Results of the fuses of Planar type P2 with different thickness.

| Thickness | Sample label | $R_0$ (Ω) | $\varepsilon_{2R0}$ (με) | $\varepsilon_{10R0}$ (με) | $\varepsilon_{20R0}$ (με) |
|---|---|---|---|---|---|
| T1 ($t_f$ = 100 nm) | P2T1_S1 | 133.60 | 2050 | 2400 | 7500 |
| | P2T1_S2 | 148.60 | 1950 | 2500 | 2950 |
| | P2T1_S3 | 152.90 | 2050 | 2100 | 2600 |
| | P2T1_S4 | 99.18 | 2500 | 5400 | 4800 |
| | P2T1_S5 | 88.59 | 2050 | 2400 | 4200 |
| | mean | 124.57 | 2120 | 2960 | 4410 |
| | std | 29.16 | 217 | 1372 | 1946 |
| | cov | 23% | 10% | 46% | 44% |
| T2 ($t_f$ = 200 nm) | P2T2_S1 | 29.66 | 3200 | — | — |
| | P2T2_S2 | 31.55 | 3900 | — | — |
| | P2T2_S3 | 74.03 | 4000 | — | — |
| | P2T2_S4 | 30.30 | 2500 | — | — |
| | P2T2_S5 | 12.76 | 5500 | — | — |
| | mean | 35.66 | 3820 | — | — |
| | std | 22.79 | 1117 | — | — |
| | cov | 64% | 29% | — | — |
| T3 ($t_f$ = 300 nm) | P2T3_S1 | 126.50 | 1200 | 2050 | 2250 |
| | P2T3_S2 | 69.13 | 1200 | 2550 | 4200 |
| | P2T3_S3 | 54.74 | 1600 | 2800 | 4650 |
| | P2T3_S4 | 40.40 | 1700 | 2500 | 3150 |
| | P2T3_S5 | 75.02 | 1250 | 2300 | 3000 |
| | mean | 73.16 | 1390 | 2440 | 3450 |
| | std | 32.70 | 241 | 282 | 966 |
| | cov | 45% | 17% | 12% | 28% |

The behavior of titanium fuses in the T2 thickness category are also documented in Table 5. By comparing planar type P1, P2 and P3 with different lengths (with $t_f$=200 nm and $w_f$=0.5 mm held constant), it is observed that the designed strain level ($\varepsilon_d$ or $\varepsilon_{2R0}$) decreases slightly with increasing length with mean values of 3820με ($l_f$=0.1 mm), 3820με($l_f$=1 mm) and 3040με($l_f$=2 mm), respectively. By comparing planar type P4, P2 and P5 with different widths (with $l_f$=1 mm and $t_f$=200 nm held constant), it is hard to conclude the influence of increasing widths on the designed strain level ($\varepsilon_d$ or $\varepsilon_{2R0}$) with mean values of 5020με($w_f$=0.1 mm), 3820με($w_f$=0.5 mm) and 5190με($w_f$=1 mm), respectively.

TABLE 5

Results of the fuses of thickness type T2 with different planar types.

| Planar type | Sample label | $R_0$ (Ω) | $\varepsilon_{2R0}$ (με) | $\varepsilon_{10R0}$ (με) | $\varepsilon_{20R0}$ (με) |
|---|---|---|---|---|---|
| P1 ($l_f$ = 0.1 mm, $w_f$ = 0.5 mm) | P1T2_S1 | 5.8 | 3600 | 9500 | — |
| | P1T2_S2 | 5.62 | 3600 | — | — |
| | P1T2_S3 | 4.94 | 2900 | 5700 | — |
| | P1T2_S4 | 5.74 | 2900 | 9300 | — |
| | P1T2_S5 | 6.57 | 6100 | — | — |
| | mean | 5.72 | 3820 | 8167 | — |
| | std | 0.56 | 1322 | 2139 | — |
| | cov | 10% | 35% | 26% | — |

TABLE 5-continued

Results of the fuses of thickness type T2 with different planar types.

| Planar type | Sample label | $R_0$ (Ω) | $\varepsilon_{2R0}$ (με) | $\varepsilon_{10R0}$ (με) | $\varepsilon_{20R0}$ (με) |
|---|---|---|---|---|---|
| P3 ($l_f$ = 2 mm, $w_f$ = 0.5 mm) | P3T2_S1 | 101.7 | 2800 | — | — |
| | P3T2_S2 | 113.3 | 2400 | — | — |
| | P3T2_S3 | 44.36 | 3700 | — | — |
| | P3T2_S4 | 63.77 | 2000 | 3000 | 3800 |
| | P3T2_S5 | 28.75 | 4300 | — | — |
| | mean | 70.38 | 3040 | — | — |
| | std | 36.32 | 945 | — | — |
| | cov | 57% | 31% | — | — |
| P4 ($l_f$ = 1 mm, $w_f$ = 0.5 mm) | P4T2_S1 | 73.77 | 5500 | 6400 | 8300 |
| | P4T2_S2 | 59.38 | 10000 | — | — |
| | P4T2_S3 | 82.5 | 2900 | 4050 | 5050 |
| | P4T2_S4 | 101.8 | 3100 | 3200 | 4000 |
| | P4T2_S5 | 62.04 | 3600 | — | — |
| | mean | 75.90 | 5020 | 4550 | 5783 |
| | std | 17.20 | 2968 | 1658 | 2242 |
| | cov | 23% | 59% | 36% | 39% |
| P5 ($l_f$ = 1 mm, $w_f$ = 1 mm) | P5T2_S1 | 73.81 | 3100 | — | — |
| | P5T2_S2 | 36.26 | 3000 | 4200 | 9800 |
| | P5T2_S3 | 58.07 | 3700 | — | — |
| | P5T2_S4 | 79.58 | 10000 | — | — |
| | P5T2_S5 | 11.01 | 6150 | — | — |
| | mean | 51.75 | 5190 | — | — |
| | std | 28.29 | 2977 | — | — |
| | cov | 55% | 57% | — | — |

The configuration of the fuse of the disclosed sensors may vary from the five samples addressed above. The tests conducted are only monotonic tensile strain tests because a study on hysteresis behavior is not required for designing a hoop strain sensor for the osseointegration application (i.e., bone growth is only monotonically increasing). However, the fuse of the disclosed sensors may be useful in other applications, e.g., in which the tensile strain is not necessarily monotonically increasing.

An example of a thin film sensor device having both sensor circuits was fabricated and simulated based on the above-described experimental characterization of the various circuit components. The circuit of the sensor configured to measure strain in the bone had an inductive element with $D_{out}$=16.925 mm, w=500 μm, s=75 μm, and n=10, resulting in an inductance and resistance of $L_{ind}$=1.386 μH and $R_{ind}$=0.934Ω, respectively. The capacitor integrated within that circuit had a nominal size of 9 mm×9 mm (with an effective size of 7.70 mm×7.70 mm governed by the top gold electrode) and polyimide dielectric thickness of 10 μm. This size capacitor had a capacitance of $C_{cap1}$=178.48 pF. The size of the inductor and capacitor are selected to attain a specific resonant frequency associated with the RLC circuit.

The other circuit for hoop strain measurement included an identical inductor as the first. However, to attain a distinct resonant frequency from the first RLC circuit, the capacitor in the second circuit haD a nominal size of 7 mm×7 mm (with an effective size 5.55 mm×5.55 mm governed by the top gold plate) and polyimide dielectric thickness of 10 μm, resulting in a capacitance of $C_{cap2}$=92.73 pF.

The resistive fuse element was designed to be 0.1 mm×0.1 mm in area and 200 nm thick, as shown in FIG. 9(*a*). The initial, pre-yield resistance of the titanium element was measured to be $R_{fuse}$=15Ω. The final prototype fabricated with the aforementioned geometries is presented in FIG. 10(*a*). To read the thin film wireless strain sensor, an inductive element with an inductance of $L_{reader}$=5 μH and resistance $R_{reader}$=0.1Ω was attached to the impedance analyzer to couple with the strain sensor.

An analysis of the sensor device was performed in MATLAB to simulate its performance under applied strain. First, the unstrained impedance of the wireless strain sensor was simulated. The impedance analyzer was simulated to sweep from 0.5 to 20 MHz. The sensor-reader coupled impedance phase (θ) and magnitude (|Z|) was simulated by adding the responses of the impedance of the reader (without the sensor present) and the two RLC circuits of the sensor:

$$\theta = \theta_{reader} + \alpha\theta_{RLC1} + \alpha\theta_{RLC2} \tag{8}$$

where α is a proportionality ratio of the two RLC circuit impedances due to the distance between the reader and the sensor. In this case, the ratio α decreases with increasing distance between the reader inductor and the thin film wireless strain sensing system. As shown in FIG. 11(*a*), the phase (θ) response due to the sweeping frequency shows the resonant frequencies of the two RLC circuits. The resonant frequency of an RLC circuit is, $$f_r = \frac{1}{2\pi\sqrt{LC}} \tag{9}$$

For the given inductance and capacitances of the two circuits, the resonant frequencies are theoretically at $f_{r1}$=10.1 MHz and $f_{r2}$=14.0 MHz. As anticipated, the two resonant frequencies are not very distinguishable in the magnitude (|Z|) plots of FIG. 11(*b*), especially when they are closer to each other. Hence, the phase θ may be chosen over the magnitude |Z| as the feature space for identifying the resonant frequency of the RLC circuits.

Planar strain was simulated in the wireless strain sensor substrate assuming it is bonded to a PVC coupon loaded under uniaxial tension with free boundary conditions in the orthogonal direction (e.g. $\sigma_x$=0 and $\sigma_y$≠0). By using equation (6), the gage factor for the capacitor, GFc, under such strain condition is calculated ($GF_c$=0.83 for PVC). This allows the strain induced capacitance to be calculated as:

$$C(\varepsilon) = C_0 + \frac{\partial C}{\partial \varepsilon}\delta\varepsilon = C_0 + GF_C \cdot C_0 \cdot \delta\varepsilon \tag{10}$$

where C is the capacitance of the capacitor as a function of applied strain, E, given the initial capacitance, $C_0$, and gage factor, $GF_c$. Using the phase peak of the RLC circuit, a gage factor for the resonant frequency can also be formulated. The RLC circuit resonant frequency gage factor, $GF_{RLC}$, is defined as:

$$GF_{RLC} = \frac{\partial f_r}{f_r\partial\varepsilon} = -\frac{1}{2}\frac{\partial C}{C\partial\varepsilon} = -\frac{1}{2}GF_C \tag{11}$$

Hence, the relationship between $df_r$ and dε is defined as:

$$GF_{RLC} = \frac{\partial f_r}{f_r\partial\varepsilon} = -\frac{1}{2}\frac{\partial C}{C\partial\varepsilon} = -\frac{1}{2}GF_C \tag{12}$$

where $df_r$ and dε are the resolutions of the resonant frequency and the strain, respectively. Assuming the wireless strain sensor is bonded to a PVC coupon, the $GF_{RLC}$ is −0.415 and if 1000με is applied to the sensor, the first resonant frequency which is nominally at 10.1 MHz would see the resonant frequency change $df_r$=−4.2 kHz. This was simulated in MATLAB as shown in FIG. 12. In the simulation, strain applied to the wireless strain sensor bonded to a PVC coupon ranged from −4000με to 4000με with a 1000με step. The phase of the first RLC circuit is plotted in FIG. 12(*a*) for the −4000, 0 and 4000με cases, while FIG. 12(*b*) plots the extracted resonant peak frequency as a function of applied strain.

FIG. 12(*c*) shows the phase impedance plots with various resistances of the fuse ($R_0$, $2R_0$, $10R_0$). The second RLC circuit of the wireless strain sensor is also explored for varying changes in resistance associated with large strain events. In this simulation, the resistance of the fuse element is changed from $R_0$ to $20R_0$ to simulate the monotonically increasing hoop strain in the second RLC circuit. As shown in FIG. 12(*c*), the absolute phase difference between the second valley and a reference point ($f_0$=1.1 MHz), |θ ($f_{r2}$)−θ (f0)|, can serve as a good indicator for threshold hoop strain. There is a nonlinear feature to the curve in FIG. 12(*d*) as expected from the nonlinear behavior of the resistive element.

Testing of a phase-based approach to interrogation, or readout, was conducted in connection with a fabricated example of the disclosed sensors shown in FIG. 10(*a*). The sensor device was interrogated using a read inductor connected to an impedance analyzer. The reactive phase response of the two RLC circuits was measured by the impedance analyzer under a sweep of AC frequencies. Valley features are present in the phase Bode plots around the resonant frequencies in FIG. 10(*b*). The results of FIG. 10(*b*) show the phase response of the read inductor with and without the sensor device in the measurement range of the read inductor. As the read inductor is moved near the sensor device, the two valleys in the phase response corresponding to the resonant frequencies ($f_{r1}$ and $f_{r2}$) are visible. The resonant frequencies are similar to the simulated results.

As shown in FIG. 13(*a*), a femur bone model was used with the conformable strain sensing system bonded to its surface. FIG. 13(*b*) shows the impedance response data obtained by the coil reader with the phase of the resonant frequency shown. As expected, as the reader is moved away from the thin film sensor device, the magnitude of the peak reduces for the same level of energy provided by the impedance analyzer. The phase magnitude of the RLC circuit with the variable capacitance is not critical in this application since the bone strain measurement is modulated on the first resonant frequency, which is detectable even as the magnitude reduces. The tests validate the ability of the reader to inductively couple with the sensor even though the sensor is mounted to a complex bone surface.

The resonant frequency corresponding to the RLC circuit with the variable capacitance may be utilized for precision strain sensing. Strain is calculated using the shift of the resonant frequency, which is affected by the strain-induced change in capacitance. In order to obtain a precise resonant frequency from measured phase response, the valley of the phase magnitude is fit (as shown in FIG. 14(*a*)) using Gauss functions at the resonant frequency. As shown in FIG. 14(*b*), the strain induced capacitance change may be detected from the phase valley with the results indicating a near linear relationship between the measured resonance frequency and the applied strain. Linear regression is performed on the resonant frequency versus strain curve resulting in an R-squared value of 0.982. Thus, the RLC circuit with the variable capacitance is validated as a good indicator for strain with a sensitivity of 4.555 Hz/μΣ.

Measurements of hoop strain using the fuse-based RLC circuit were also obtained. A gradually increasing tensile strain was applied to approximately 10,000με with a step size of about 1,000με to mimic hoop strain as bone growth occurs in an osseointegrated implant (e.g., as shown in FIG. 1(*b*)). The phase valley corresponding to the RLC circuit is expected to broaden and in effect disappear as the fuse fails under large strain.

The signal from the reader alone (background) is first subtracted from the raw data, which is obtained when the read inductor is interrogating near the sensor. As shown in FIG. 14(*c*), the resulting impedance phase plot is then normalized by shifting it to start from a 90° phase at 6.0 MHz. This normalization stage is implemented to enhance the visualization of changes in impedance phase as large strain is experienced. Valley fitting is again performed using a Gauss function in order to obtain an accurate measurement of the RLC circuit resonance frequency.

At each loading step, the two valleys are observed by sweeping the frequency using the impedance analyzer over a wide range (e.g., 6 MHz-18 MHz). Then the data around each valley is collected with more precision by sweeping over a narrower frequency range. The first valley from the first RLC circuit is shown in FIG. 14(*c*) from 9.0 MHz to 11 MHz and the second valley from the second RLC circuit is shown in FIG. 14(*d*) from 11 MHz to 17 MHz. The plots in FIGS. 14(*c*) and (*d*) have been normalized by subtracting from the coupled impedance the impedance of the reader and by shifting the impedance phase plots to start at 90° at 9.0 MHz and 11 MHz, respectively. The results shown in FIGS. 14(*d*) and (*e*) reveal the phase valley of the hoop strain RLC circuit generally broadens and decreases under increasing tensile strain starting at 4000με. In this specimen, the fuse fails at around 6600με. FIG. 14(*e*) shows the plot of the absolute phase difference between the second valley and the reference point ($|\theta(f_{r2})-\theta(f_0)|$) versus monotonically increasing strain. The abrupt drop starting from around 5000με to 6000με indicates the efficiency of using the absolute phase difference $|\theta(f_{r2})-\theta(f_0)|$ as an efficient indicator for representing large threshold hoop strain in osseointegration applications. Two other samples of the sensing systems were tested, showing fuse failure at similar strains. The results illustrate that the disclosed sensors and systems provide a useful tool for monitoring the bone growth in osseointegrated prosthesis applications.

FIG. 15 depicts an example of a method 1500 of sensing hoop strain in connection with an object. The object may be growing, such as in connection with bone growth, or otherwise undergoing peripheral (e.g., circumferential) expansion. The method 1500 may be implemented using one of the above-described sensors or sensor devices, or one of the above-described sensor systems.

The method 1500 may begin with an act 1502 in which a strain sensor is applied around a periphery of the object. The strain sensor includes a flexible substrate and a circuit disposed on the flexible substrate. As described above, the circuit includes an inductance and an elongated trace coupled to the inductance. The elongated trace bends as the strain sensor is applied around the periphery of the object. The elongated trace includes a non-uniformity configured such that the elongated trace tears at the non-uniformity and exhibits a non-linear increase in resistance as the hoop strain reaches a strain threshold.

In an act 1504, an excitation signal is directed to the inductance. The excitation signal may be a radio frequency or other electromagnetic signal. The excitation signal causes the circuit to generate a radio frequency response via the inductance of the circuit.

The radio frequency response is monitored in an act 1506 for a change in a characteristic of the radio frequency response to detect the non-linear increase in the resistance. As described above, the characteristic may be a phase of the radio frequency response in some cases. Additional or alternative response characteristics may be used, including, for instance, a magnitude of the response.

In some cases, the act 1502 includes affixing ends of an elongated strip of the flexible substrate to the object. As described above, the elongated trace may be disposed on the elongated strip. The elongated strip may or may not extend entirely around the periphery of the object. Alternatively or additionally, the sensor may be wrapped in an act 1510 around the object. In some cases, the sensor is wrapped around the entire periphery of the object such that ends of the sensor may overlap. The overlap allows the sensor to be affixed to itself, e.g., by fastening ends of the flexible substrate to one another. The manner in which the ends are affixed to the object or to one another may vary.

The act 1504 may include an act 1512 in which the excitation signal is generated across a range of frequencies. For instance, the excitation signal may sweep or otherwise vary across the range of frequencies. For example, the frequency may change in a discontinuous manner for excitation at discrete frequencies within the frequency range.

The act 1506 may include evaluating the radio frequency response in an act 1514 to detect when the change in the characteristic of the radio frequencies occurs. In the phase-based example, the evaluation may include or involve identifying the frequency at which a valley in the phase response decreases.

Described above are passive wireless strain sensing sensor devices and systems. Thin film fabrication methods have also been described to fabricate the passive resistive, inductive, capacitive, and other elements of the circuits of the disclosed sensors. In some cases, the disclosed sensors provide multifunctional strain sensing, including, for instance, measuring low level bone strain and high levels of hoop strain associated with bone growth. Thin film circuit components, including parallel plate capacitors, square coil inductors and miniaturized resistive fuses, are fabricated and patterned using, e.g., biocompatible materials and lithographic processing techniques. The disclosed sensors are capable of in situ monitoring of the growth, load response and condition of human bone. The bone monitoring provided by the disclosed sensors supports the deployment of osseointegrated mechanical components fixated into bone, such as artificial joints and osseointegrated prosthetic limbs. The strain sensors provide a bio-compatible wireless inductive strain sensing system configured to monitor the growth and strain response of bone hosting implants.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. A strain sensor comprising:

a flexible substrate; and a circuit disposed on the flexible substrate, the circuit comprising an inductance to receive an excitation signal, the circuit being configured to generate a radio frequency response to the excitation signal via the inductance;

wherein the circuit comprises an elongated trace coupled to the inductance and configured to bend and stretch longitudinally upon deformation of the flexible substrate, the elongated trace comprising a non-uniformity configured such that the elongated trace deforms and tears at the non-uniformity and exhibits a non-linear increase in resistance as a tensile strain to which the elongated trace is subjected reaches a strain threshold;

wherein the non-linear increase in resistance modifies a characteristic of the radio frequency response of the circuit.

2. The strain sensor of claim 1, wherein the non-uniformity comprises a non-uniform composition of the trace.

3. The strain sensor of claim 1, wherein the non-uniformity comprises a non-uniform thickness of the trace.

4. The strain sensor of claim 1, wherein:

the elongated trace comprises a plurality of metal layers; and at least one metal layer of the plurality of metal layers is not present at the non-uniformity.

5. The strain sensor of claim 1, wherein:

the elongated trace comprises a conduction metal layer and an adhesion metal layer disposed between the conduction metal layer and the flexible substrate; and the conduction metal layer is not present at the non-uniformity such that the elongated trace has a thickness at the non-uniformity that corresponds with a thickness of the adhesion metal layer.

6. The strain sensor of claim 1, wherein the trace is disposed along a curve arising from the deformation of the flexible substrate such that the tensile strain is a hoop strain.

7. The strain sensor of claim 1, wherein the characteristic of the radio frequency response is a phase of the radio frequency response generated by the circuit in response to the excitation signal.

8. The strain sensor of claim 1, further comprising a further circuit disposed on the flexible substrate, the further circuit comprising an inductor and a capacitor, wherein:

the inductor is configured to receive the excitation signal;

the capacitor comprises a parallel plate arrangement; and the parallel plate arrangement is configured such that a radio frequency response of the further circuit to the excitation signal is modified by strain arising from further deformation of the substrate and the capacitor.

9. The strain sensor of claim 1, wherein the circuit further comprises a capacitance, both the inductance and the capacitance being disposed in series with the elongated trace.

10. The strain sensor of claim 9, wherein the inductance and the capacitance are positioned such that the deformation of the flexible substrate does not modify the inductance and the capacitance.

11. The strain sensor of claim 1, wherein the flexible substrate comprises a section on which the inductance is disposed and an elongated strip extending outward from the section, the elongated trace being disposed on the elongated strip.

12. The strain sensor of claim 11, wherein the elongated trace comprises a conductive loop disposed on the elongated strip.

13. The strain sensor of claim 11, wherein the flexible substrate comprises a biocompatible polymer substrate.

14. A method of sensing hoop strain in connection with an object, the method comprising:

applying a strain sensor around a periphery of the object, the strain sensor comprising:

a flexible substrate; and a circuit disposed on the flexible substrate, the circuit comprising an inductance, the circuit comprising an elongated trace coupled to the inductance, the elongated trace bending as the strain sensor is applied around the periphery of the object, the elongated trace comprising a non-uniformity configured such that the elongated trace tears at the non-uniformity and exhibits a non-linear increase in resistance as the hoop strain reaches a strain threshold;

directing an excitation signal to the inductance, the excitation signal causing the circuit to generate a radio frequency response via the inductance; and monitoring the radio frequency response for a change in a characteristic of the radio frequency response to detect the non-linear increase in the resistance.

15. The method of claim 14, wherein applying the strain sensor comprises affixing ends of an elongated strip of the flexible substrate to the object, the elongated trace being disposed on the elongated strip.

16. The method of claim 14, wherein:

directing the excitation signal comprises generating the excitation signal across a range of frequencies; and monitoring the radio frequency response comprises evaluating the radio frequency response to detect when the change in the characteristic of the radio frequencies occurs.

17. The method of claim 14, wherein the characteristic of the radio frequency response comprises a phase of the radio frequency response.

18. The method of claim 14, wherein applying the strain sensor comprises wrapping the strain sensor around a bone such that the hoop strain is indicative of circumferential bone growth.

* * * * *